US006214562B1

(12) United States Patent
Weng et al.

(10) Patent No.: US 6,214,562 B1
(45) Date of Patent: Apr. 10, 2001

(54) TRANSCRIPTIONALLY REGUALTED G PROTEIN-COUPLED RECEPTOR

(75) Inventors: Zhigang Weng, Cambridge, MA (US); Owen N. Witte, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/120,025

(22) Filed: Jul. 17, 1998

Related U.S. Application Data

(63) Continuation-in-part of application No. 08/969,815, filed on Nov. 13, 1997.

(51) Int. Cl.$^7$ .......................... G01N 33/50; C12N 15/12; C12N 15/63

(52) U.S. Cl. .......................... 435/7.1; 435/7.2; 435/7.21; 435/69.1; 435/325; 435/172.3; 435/252.3; 536/24.3; 536/23.1

(58) Field of Search ..................................... 435/7.2, 7.21, 435/7.1, 69.1, 325, 172.3, 252.3; 536/24.3, 23.1; 530/350, 300

(56) References Cited

PUBLICATIONS

Rudinger, J et al., Peptide Hormones, ed. J. A. Parsons, University Park Press, Baltimore, pp. 1–7, 1987.*

Watson, S. et al., The G–Protein Linked Receptor Facts Book, Academic Press, pp. 2–6, 1994.*

Afar, et al., "Differential Complementation of Bcr–Abl Points Mutants with c–Myc", *Science*, 164 :424–426 (Apr. 15, 1994).

Afar, et al., "Signaling by ABL oncogenes through cyclin D1", *Proc. Natl. Acad. Sci. USA*, 92 :9540–9544 (Oct. 1995).

Alkhatib, et al, "CC CKR5: A Rantes, MIP–1β Receptor as a Fusion Cofactor for Macrophage–Tropic HIV–1", *Science*, 272 :19551958 (Jun. 28, 1996).

Arvanitakis, et al., "Human herpesvirus KSHV encodes a constitutively active G–protein–coupled receptor linked to cell proliferation", *Nature*, 385 :347–350 (Jan. 23, 1997).

Braun, et al., "Identification of Target Genes for the Ewing's Sarcoma EWS/FLI Fusion Protein by Representational Difference Analysis", *Molecular and Cellular Biology*, 15(8):4623–4630 (Aug. 1995).

Choe, et al., "The β–Chemokine Receptos CCR3 and CCR5 Facilitate Infection by Primary HIV–1 Isolates", *Cell*, 85 :1135–1148 (Jun. 28, 1996).

Davis, R.J., "Transcriptional Regulation by MAP Kinases", *Molecular Reproduction and Development*, 42 :459–467 (1995).

Deng, et al., "Identification of a major co–receptor for primary isolates of HIV–1", *Nature*, 381 :661–666 (Jun. 20, 1996).

Choi, et al., "Identification of a Putative G Protein–Coupled Receptor Induced during Activation–Induced Apoptosis of T Cells", *Cellular Immunology*, 168 :78–84 (1996).

Doranz, et al., "A Dual–Topic Primary HIV–1 Isolate That Uses Fusin and the β–Chemokine Receptors CKR–5, CKR–3, and CKR–2b as Fusion Cofactors", *Cell*, 85:1148–1158 (Jun. 28, 1996).

Dragic, et al., "HIV–1 entry into CD4$^+$ cells is mediated by the chemokine receptor CC–CKR–5", *Nature*, 381 :667–673 (Jun. 20, 1996).

Feng, et al., "HIV–1 Entry Cofactor: Functional cDNA Cloning of a Seven–Transmembrane, G Protein–Coupled Receptor", *Science*, 272 :872–877 (May 10, 1996).

Förster, et al., "A Putatuve Chemokine Receptor, BLR1, Directs B Cell Migration to Defined Lymphoid Organs and Specific Anatomic Compartments of the Spleen", *Cell*, 87 :1037–1047 (Dec. 13, 1996).

Fu, M.L.X. "Characterization of anti–heart M2 muscarinic receptor antibodies—a combined clinical and experimental study", *Molecular and Cellular Biochemistry*, 163/164 :343–347 (1996).

Goga, et al., "Alternative Signals to RAS for Hematopoietic Transformation by the BCR–ABL Oncogene", *Cell*, 82 :981–988 (Sep. 22, 1995).

Hubank, et al., "Identifying differences in mRNA expression by representational difference analysis of cDNA", *Nucleic Acids Research*, 22(25) :5640–5648 (1994).

Koshiba, et al., "Transient up–regulation of P2Y$_2$ nucleotide receptor mRNA expression is an immediate early gene response in activated thymocytes", *Proc. Natl. Acad. Sci. USA*, 94 :831–836 (Feb. 1997).

Kurzrock, et al., "The Molecular Genetics of Philadelphia Chromosome—Positivie Leukemias", *The New England Journal of Medicine*, 319(15) :990–998 (Oct. 13, 1988).

Lugo, et al., "The BCR0ABL Oncogene Transforms Rat–1 Cells and Cooperates with v–myc", *Molecular and Cellular Biology*, 9(3) :1263–1270 (Mar. 1989).

McLaughlin, et al., "Alternative Forms of the BCR–ARL Oncogene Have Quantitatively Different Potencies for Stimulation of Immature Lymphoid Cells", *Molecular and Cellular Biology*, 9(5) :1866–1874 (May 1989).

Muller, et al., "BCR First Exon Sequences Specifically Activate the BCR/ABL Tyrosine Kinase Oncogene of Philadelphia Chromosome–Positive Human Leukemias", *Molecular and Cellular Biology*, 11(4) :1785–1792 (Apr. 1991).

(List continued on next page.)

*Primary Examiner*—Yvonne Eyler
*Assistant Examiner*—Nirmal S. Basi
(74) *Attorney, Agent, or Firm*—Gates & Cooper LLP

(57) ABSTRACT

A G protein-coupled receptor (GPCR), called G2A, whose expression is regulated and functions at the G2/M checkpoint to ensure properly controlled duplication of hematopoietic cells. The receptor is found predominantly in hematopoietic cells and tissues and functions as a tumor suppressor gene and induces cell cycle arrest. This receptor may play an important role in regulating the proliferation and differentiation of hematopoietic cells. Regulation of receptor activity has several therapeutic applications.

12 Claims, 15 Drawing Sheets

OTHER PUBLICATIONS

Murphy, P.M., "The Molecular Biology of Leukocyte Chemoattractant Receptors", *Annu. Rev. Immunol.*, 12 :593–633 (1994).

Pear, et al., "Production of high–titer helper–free retroviruses by transient transfection", *Proc. Natl. Acad. Sci. USA*, 90 :8392–8396 (Sep. 1993).

Pendergast, et al., "BCR–ABL–Induced Oncogenesis Is Mediated by Direct Interaction with the SH2 Domain of the GRB–2 Adaptor Protein", *Cell*, 75 :175–185 (Oct. 8, 1993).

Schneider, et al., "Genes Specifically Expressed at Growth Arrest of Mammalian Cells", *Cell*, 54 :787–793 (Sep. 9, 1988).

Strader, et al., "The familey of G–protein–coupled receptors", *The FASEB Journal*, 9 :745–754 (Jun. 1995).

Strader, et al., "Structure and Function of G Protein–Coupled Receptors", *Annu. Rev. Biochem.*, 63 :101–132 (1994).

Tsukada, et al., "Deficient Expression of a B Cell Cytoplasmic Tyrosine Kinase in Human X–Linked Agammaglobulinemia", *Cell*, 72 :279–290 (Jan. 29, 1993).

Lisitsyn, et al., "Cloning the Differences Between Two Complex Genomes", *Science*, 259 :946–951 (Feb. 12, 1993).

Libert, et al., "Selective Amplitication and Cloning at Four New Members fo the G Protein–Coupled Receptor Family", *Science*, 244:569–572 (1989).

Bouvier, et al., "Dynamic Palmitoylation of G–Protein–Coupled Receptors in Euraryotic Cells" *Methods in Envymology, Academic Press*, pp. 300–314.

\* cited by examiner

Alignment of Mouse and Human GPCRs

```
  1  MRSEPTNAAGNTTLGVTSVLQSTSVPSSETCHVSYEESRVVLVVVYSAVC   50  Mouse
     |      .:..|.:..|...:.| ::......:||:||||:||||||||||
  4  MLLKNGYNGNATPVTTTAPWASLGLSAKTCNNVSFEESRIVLVVVYSAVC   53  Human 51  LLGLPANCLTAWLTLLQVLQRNVLAVYLFCLSLCELLYISTVPLWIIYIQ  100  Mouse
     ||:||||||||||.||||||  ||||||:||.||||||..:|:|||:|||.
 54  TLGVPANCLTAWLALLQVLQGNVALVYLLCLALCELLYTGTLPLWVIYIR  103  Human 101  NQHKWNLGPQACKVTAYIFFCNIYISILLLCCISCDRYMAVVYALESRGH  150  Mouse
     |||:|.||   |||||||||||||||:|||:|||||||::|||||||||:
104  NQHRWTLGLLACKVTAYIFFCNIYVSILFLCCISCDRFVAVVYALESRGR  153  Human 151  RHQRTAVTISACVILLVGLVNYPVFDMKVEKSFCFEPLRMNSKIAGYHYL  200  Mouse
     |:.|||: ||||:::|||:|:||||:  :|. ||: |.|:|:||||.|
154  RRRRTAILISACIFILVGIVHYPVFQTE.DKETCFDMLQMDSRIAGYYYA  202  Human 201  RFTFGFAIPLGILAFTNHQIFRSIKLSDSLSAAQKNKVKRSAIAVVTIFL  250  Mouse
     |||.||||||:|:|||||.||||||||   :||||||.|||:||||||.|||
203  RFTVGFAIPLSIIAFTNHRIFRSIKQSMGLSAAQKAKVKHSAIAVVVIFL  252  Human 251  VCFAPYHVVLLVKAASFSFYQGDMDAVCAFESRLYTVSMVFLCLSTVNSV  300  Mouse
     |||||||:||||||||.||.:|:||..:|:|::|.||||.|:|||||||||:|
253  VCFAPYHLVLLVKAAAFSYYRGDRNAMCGLEERLYTASVVFLCLSTVNGV  302  Human 301  ADPIIYVLGTDHSRQEVSRIHTGWKKWSTKTYV...TCSKDSEETHLPTE  347  Mouse
     |||||||||:||||||||||||.|||.|||  | :|.||   |:|.||  :|..
303  ADPIIYVLATDHSRQEVSRIHKGWKEWSMKTDVTRLTHSRDTEELQSPVA  352  Human 348  LSNTYTFPNPAHPPGSQPAKLGLLCSPERLPEELC  382                Mouse
     |.:|||..|.||||.          |.:|| ||| |
353  LADHYTFSRPVHPPGSP.......CPAKRLIEESC  380                Human
```

FIG. 5

COUNTER-SELECTION OF G2A IN TRANSFORMED PRE-B CELLS
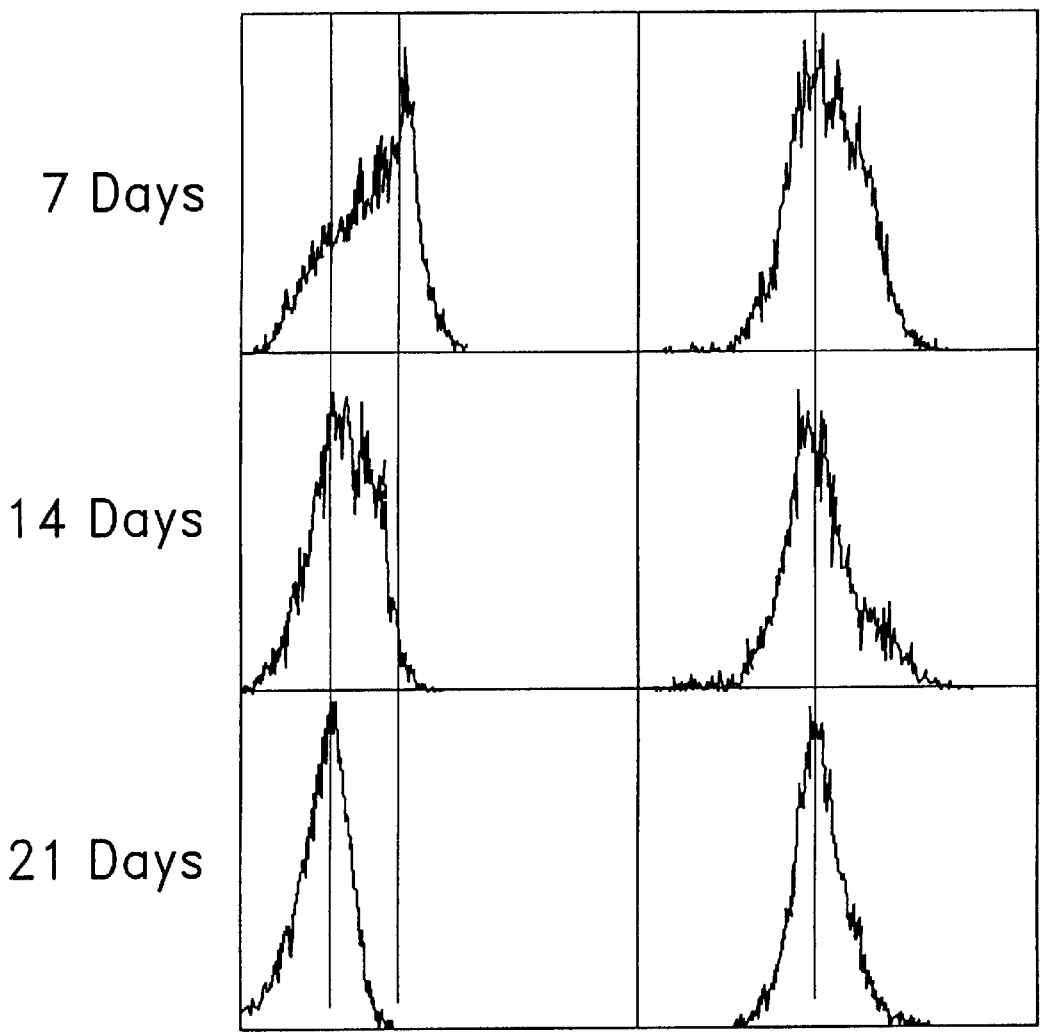
*FIG. 8*

TRANSCRIPTIONALLY REGUALTED G PROTEIN-COUPLED RECEPTOR

RELATED APPLICATIONS

This present application is a continuation-in-part of U.S. patent application Ser. No. 08/969,815, filed on Nov. 13, 1997.

GOVERNMENT SUPPORT

This invention was made with Government support under NIH Grant No. CA 53867. The Government has certain rights in the invention.

FIELD OF THE INVENTION

The present invention relates to a G protein-coupled receptor whose expression is regulated in hematopoietic cells and functions at the G2/M checkpoint to ensure properly controlled duplication of hematopoietic cells.

BACKGROUND OF THE INVENTION

The family of G protein-coupled receptors (GPCRs) has at least 250 members (Strader et al. *FASEB J.*, 9:745–754, 1995; Strader et al. *Annu. Rev. Biochem.*, 63:101–32, 1994). It has been estimated that one percent of human genes may encode GPCRs. GPCRs bind to a wide-variety of ligands ranging from photons, small biogenic amines (i.e., epinephrine and histamine), peptides (i.e., IL-8), to large glycoprotein hormones (i.e., parathyroid hormone). Upon ligand binding, GPCRs regulate intracellular signaling pathways by activating guanine nucleotide-binding proteins (G proteins). GPCRs play important roles in diverse cellular processes including cell proliferation and differentiation, leukocyte migration in response to inflammation, and cellular response to light, odorants, neurotransmitters and hormones (Strader et al., supra.).

Interestingly, GPCRs have functional homologues in human cytomegalovirus and herpesvirus, suggesting that GPCRs may have been acquired during evolution for viral pathogenesis (Strader et al., *FASEB J.*, 9:745–754, 1995; Arvanitakis et al. *Nature*, 385:347–350, 1997; Murphy, *Annu. Rev. Immunol.* 12:593–633, 1994).

The importance of G protein-coupled receptors is further highlighted by the recent discoveries that its family members, chemokine receptors CXCR4/Fusin and CCR5, are co-receptors for T cell-tropic and macrophage-tropic HIV virus strains respectively (Alkhatib et al., *Science*, 272:1955, 1996; Choe et al., *Cell*, 85:1135, 1996; Deng et al., *Nature*, 381:661, 1996; Doranz et al., *Cell*, 85:1149, 1996; Dragic et al., *Nature*, 381:667 (1996); Feng et al., *Science* 272:872, 1996). It is conceivable that blocking these receptors may prevent infection by the human immunodeficiency (HIV) virus.

Cell cycle checkpoints, intervals in the cell cycle in which the cell detects impairment or loss of integrity to its genome and arrests growth in order to make repairs, ensure that DNA is replicated with high fidelity (Paulovich et al., *Cell* 88:315–321, 1997; Hartwell, *Cell* 71:543–546, 1992). There are three separately defined times in the eukaryotic cell cycle identified as checkpoints: G1/S transition, S-phase delay and G2/M transition (Nurse, *Cell* 91:865–867, 1997). The G1/S checkpoint is activated to avoid copying mutated DNA by increasing the time available for repair. Cells also utilize a DNA damage checkpoint within S phase by slowing the rate of DNA replication. The G2/M checkpoint is activated upon detection of double-stranded DNA breaks. In addition, mitotic entry is monitored by a spindle checkpoint that inhibits anaphase progression when chromosomes are not attached to the mitotic spindle (Nicklas, *Science* 275:632–637, 1997). The cell cycle checkpoint is summarized in FIG. 1.

Recent discoveries have shed light on the molecular participants in the G2/M transition. Cdc2 and Cyclin B1 promote entry into mitosis and are part of the maturation promoting factor (MPF). Dephosphorylation of Cdc2 on Thr14 and Tyr15 by Cdc25 and phosphorylation on Thr161 concomitant with nuclear association with Cyclin B1 results in rapid entry into mitosis. Cyclin B1 degradation or export to the cytoplasm and phosphorylation of Cdc2 on the negative regulatory sites Thr14 and Tyr15 by Wee1 block entry into mitosis. Caffeine can relieve DNA damage-activated G2/M arrest by stimulating the dephosphorylation of Cdc2. These data strongly implicate MPF as the central regulator of the transition from G2 into mitosis.

Recent work has broadened our understanding of the signaling pathways involved in G2/M arrest upstream of MPF. Response to DNA damage is detected by the Ataxia Telangiectasia mutated (ATM) which is a human homologue of the yeast rad family of genes (Meyn, 1995). The ATM protein has been implicated in the activation of Chk1, which phosphorylates Cdc25, leading to binding and sequestering of Cdc25 by 14-3-3 (Sanchez et al., *Science* 277:1497–1501, 1997; Peng et al., *Science* 277:1501–1505, 1997; Furnari, *Science* 277:1495–1497, 1997). This results in accumulation of the phosphorylated (inactive) form of Cdc2 and G2/M arrest. Cds1 has been demonstrated to function redundantly to Chk-1 by phosphorylating both Wee1 and Cdc25, inactivating both gene products (Boddy et al., *Science* 280:909–912, 1998; Fumari et al, supra.; Sanchez et al., supra.). ATM serves to activate proteins that act directly on MPF and lead to cell cycle arrest.

ATM also associates with and activates proteins that stimulate transcription of secondary molecules involved in checkpoint controls. One of these downstream activators of ATM is the tumor suppressor p53. Activation of p53 leads to the induction of multiple genes, including p21Cip and 14-3-3 (Levine, *Cell* 88:323–331, 1997). The 14-3-3 gene product mediates G2M arrest by binding to Cdc25 to sequester it in the cytoplasm. The tyrosine kinase Abl physically interacts with the ATM gene product (Shafman, *Nature* 387:520–523, 1997; Baskaran, *Nature* 387:516–519, 1997). Activation of the Abl kinase by DNA damage is dependent on the ATM, suggesting a functional link of Abl and ATM in the DNA damage checkpoint regulation. The overall regulation of the G2M checkpoint is an intricate mechanism involving both post-transcriptional modifications and transcriptional activation to guarantee proper cell growth. Thus, the known G2/M checkpoint proteins ultimately function through regulation of Cdc2 phosphorylation and nuclear import of Cyclin B1.

While the general eukaryotic cell cycle control machinery is highly conserved among a broad range of cell types, little is known about tissue-specific cell cycle regulators. TGF-β and GATA-5 represent anti-proliferative signaling molecules that are restricted in expression. Both of these regulators restrict the cell cycle at G1. Lymphocytes provide an interesting model system to study tissue-specific cell cycle regulators since their development is marked by the unique property of entering, exiting and re-joining the cell cycle depending on their internal developmental stages as well as the surrounding environment. For example, upon interaction with antigen, the resting mature naive B cells accumulate in the lymphoid germinal centers in which they undergo vigorous proliferation and excess B cells die by being included from germinal centers.

Loss of cellular growth controls by oncogenic transformation is dependent on signals emanating from the oncogene to downstream signaling partners and frequently leads to transcriptional induction of secondary genes which contribute to malignant growth. BCR-ABL is a chimeric tyrosine kinase oncogene generated by a reciprocal chromosomal translocation t(9;22)(q34;q11) associated with the pathogenesis of chronic myelogenous leukemia (CML) and acute lymphocytic leukemia (ALL) (Kurzrock, *N. Engl. J. Med.* 319: 990–998, 1988). This chimeric oncogenesis found in Ph[1]-positive stem cells. Structural and functional analysis have defined critical domains within BCR-ABL responsible for its oncogenic activity. In particular, the R552L substitution within a highly conserved motif of the Src Homology 2 (SH2) domain uncouples the SH2 domain with phosphotyrosine-containing proteins without affecting the kinase activity of BCR-ABL. Interestingly, this mutation greatly reduces the ability of BCR-ABL to stimulate anchorage-independent growth of rat fibroblasts in soft agar (Goga, *Cell* 82:981–988, 1995). Although the SH2 mutant still retains the ability to transform primary bone marrow cells in vitro, it exhibits diminished malignant and leukemogenic potential in mice (Goga, supra.). Inactivation of the SH2 domain may uncouple BCR-ABL with downstream signaling molecules, which in turn may alter the expression of critical genes involved in leukemogenesis.

SUMMARY OF THE INVENTION

One embodiment of the present invention is a method of identifying a compound which activates the G protein coupled receptor G2A, comprising the steps of: contacting the G2A with a test compound; determining whether the compound binds to the G2A; and testing compounds which bind to the G2A in a receptor activity assay, whereby stimulation of receptor activity indicates that the compound is an activator of the G2A. Preferably, the G2A is expressed on the cell surface. Advantageously, the receptor activity assay is fibroblast transformation, bone marrow transformation, cell cycle analysis, in vivo tumor formation or in vivo leukemogenesis.

The present invention also provides a method of identifying a compound which inhibits G2A, comprising the steps of: contacting the G2A with a test compound; determining whether the compound binds to the G2A; and testing compounds which bind to the G2A in a receptor activity assay, whereby inhibition of receptor activity indicates that the compound is an inhibitor of the G2A. Preferably, the G2A is expressed on the cell surface. Advantageously, the receptor activity assay is fibroblast transformation, bone marrow transformation, cell cycle analysis, in vivo tumor formation or in vivo leukemogenesis.

Another embodiment of the present invention is a method for inducing cell cycle arrest in a cell, comprising contacting said cell with a compound which activates the G2A receptor. In one aspect of this preferred embodiment, the cell cycle arrest occurs at the G2/M transition of said cell cycle. Preferably, the cell is a leukemia cell or lymphoma cell.

The present invention also provides a method for determining the presence of cancer cells, comprising determining whether the cells express the G2A transcript, wherein the presence of an increased level of the transcript compared to a control cell indicates that the cell is a cancer cell. Preferably, the determining step comprises Northern hybridization or polymerase chain reaction.

Still another embodiment of the invention is a method for determining the presence of cancer cells, comprising determining whether said cells express G2A protein, wherein the presence of an increased level of the protein compared to a control cell indicates that the cell is a cancer cell. Preferably, the determining step comprises contacting the cells with an antibody specific for the G2A protein and detecting the presence of the antibody. Advantageously, the detecting step comprises fluorescence activated cell sorting (FACS).

The present invention also provides a method for inhibiting degradation of the G2A receptor in a cell, comprising contacting the cell with an inhibitor of the 20S proteosome. Preferably, the inhibitor is N-acetyl-L-leucinyl-L-leucinyl-L-norleucinal (ALLN) or N-acetyl-L-leucinyl-L-leucinyl-L-methional (ALLM).

Another embodiment of the present invention is a method for inhibiting leukemogenesis in an individual in need thereof, comprising: isolating bone marrow from said individual; transfecting or infecting said bone marrow with an expression construct encoding G2A protein; and returning said bone marrow to said individual. Preferably, the expression construct is a retroviral vector.

BRIEF DESCRIPTION OF THE DRAWINGS

FIG. 5 shows a sequence alignment of the murine SEQ ID NO: 2 and human SEQ ID NO: 4 G2As. The human and murine G2As share approximately 70% identity at the amino acid level.

FIG. 8 is a flow cytometry profile showing counter-selection of G2A in pre-B cells transformed with the G2A-GFP or GFP retroviral vectors.

DETAILED DESCRIPTION OF THE INVENTION

The present invention describes the identification and sequencing of a novel G protein-coupled receptor (GPCR), called G2A for G2 arrest, which is transcriptionally regulated by a variety of intracellular and extracellular stimuli including tyrosine linases, DNA damaging agents and chemotherapeutic drugs. G2A appears to serve as a tissue specific sensor of DNA damage and cellular proliferation, and functions at the G2/M checkpoint to delay mitosis following DNA damage, or to prevent deregulated growth incurred by excessive growth stimuli. Therefore, G2A may couple proliferative signaling and cell cycle checkpoint pathways to ensure faithful and properly controlled duplication of hematopoietic cells.

Figure 1:
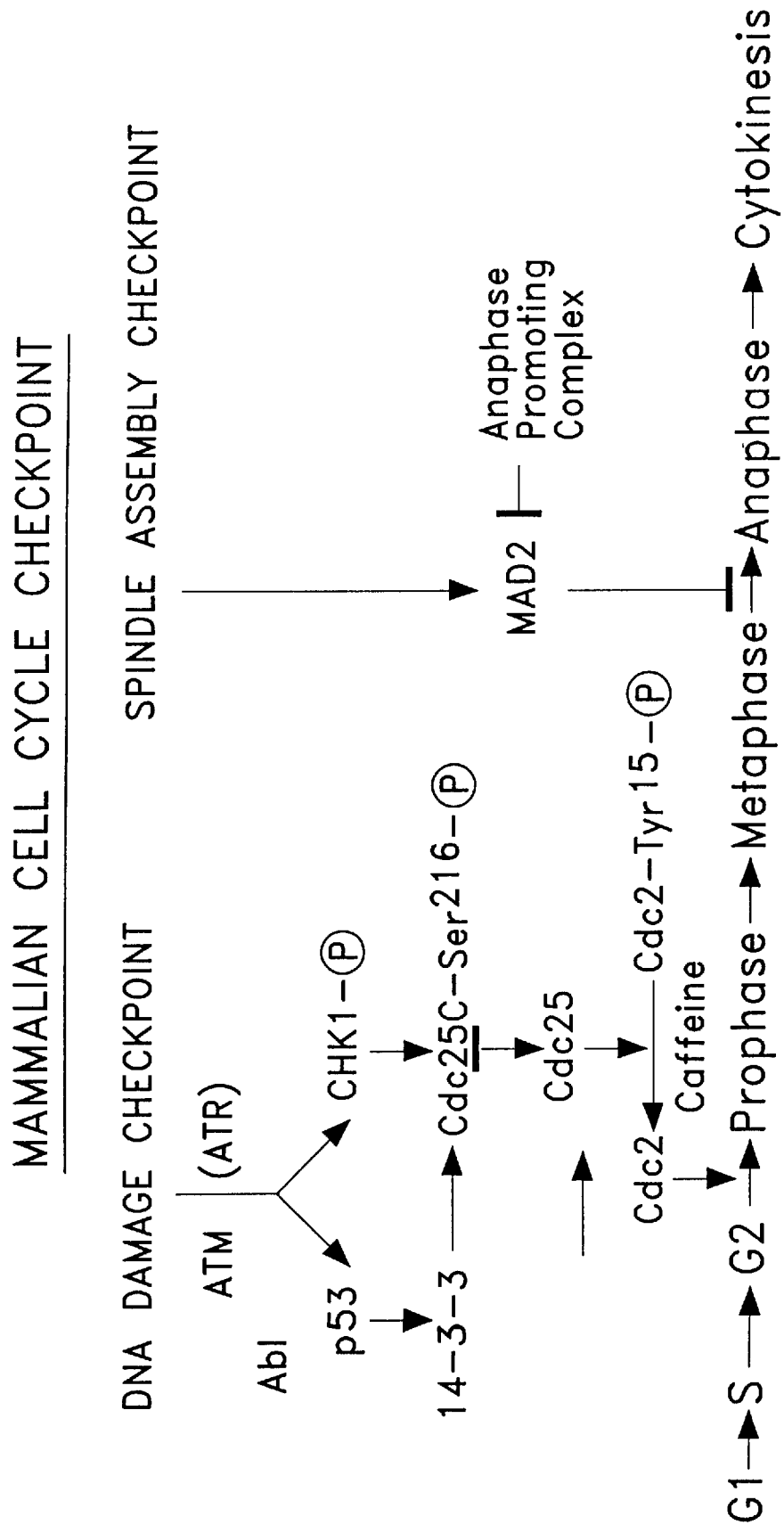
FIG. 1 is a schematic diagram showing the mammalian cell cycle checkpoint.
Figure 2:
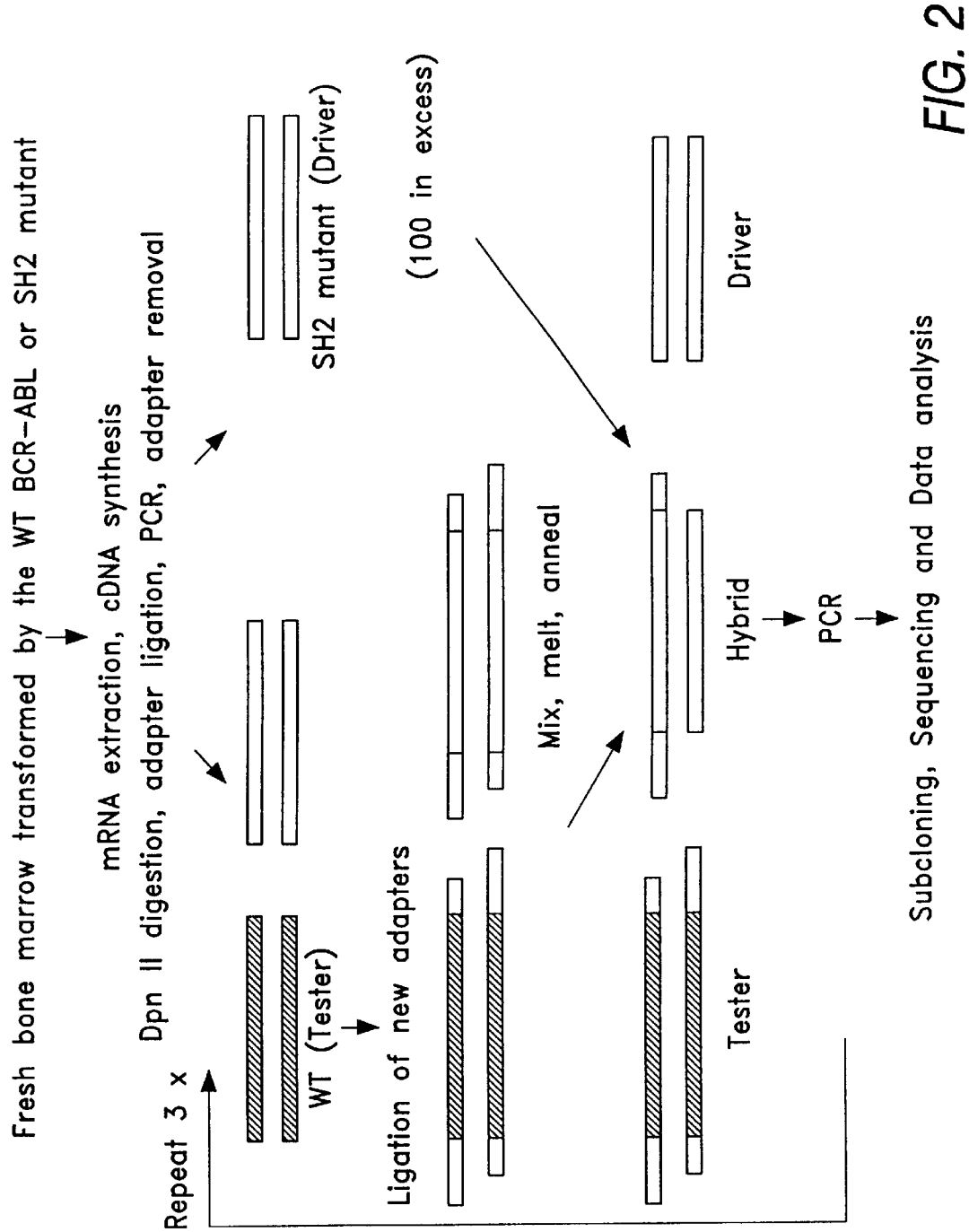
FIG. 2 is a schematic diagram depicting the isolation of differentially-expressed genes by representational difference analysis (RDA). After mRNA isolation and cDNA synthesis, tester and driver cDNAs are digested with a restriction enzyme (RE) and ligated with adapters. After PCR amplification, the adaptors are removed by RE digestion and new adaptors are ligated to the tester DNA fragments only. The tester DNA is hybridized to an excess of driver DNA. DNA fragments from differentially-expressed genes will form homodimers with the new adapters at both ends and can be exponentially amplified by PCR Fragments present in both driver efficiently amplified. The process is repeated 3–4 times and differentially amplified DNA fragments are subcloned for further analysis.

G2A functions as a tumor suppressor gene, induces cell cycle arrest during mitosis and is found on human chromosome 14q32.3, a region frequently found altered in human cancers. G2A was identified while studying cellular genes that can be regulated by BCR-ABL. Using representational difference analysis (RDA), a PCR-based differential screening technique (Lisitsyn et al., Science 259:946–951, 1993; Hubank et al., Nucl. Acids Res. 22:5640–5648, 1994; FIG. 2), genes expressed in murine bone marrow (pre-B) cells transformed by the wild type (WT) BCR-ABL were compared to those expressed when a transformation-defective mutant variant carrying a mutation in the SH2 domain of BCR-ABL was used to infect these cells. More than a dozen genes were found to be upregulated by BCR-ABL. One of these differentially expressed murine genes (G2A) was predominantly expressed in hematopoietic tissues such as spleen and thymus, and was induced by WT BCR-ABL, but not the SH2 mutant.

The cDNA and deduced amino acid sequences of the murine G2A are shown in SEQ ID NO: 1 and SEQ ID NO: 2, respectively. The human homologue of the mouse protein was then isolated using the murine cDNA as a probe. The corresponding human cDNA and deduced amino acid sequences are shown in SEQ ID NO: 3 and SEQ ID NO: 4, respectively. The G2A protein sequence of the invention has the sequence shown in SEQ ID NOS; 2 and 4, or sequence variations thereof which do not substantially compromise the ability of these genes to be regulated by protein tyrosine kinases or sequence variations thereof which do not substantially compromise the functional activities of these proteins. It will be appreciated that G2A proteins containing one or more amino acid replacements in various positions of the sequences shown in SEQ ID NOS: 2 and 4 are also within the scope of the invention.

Many amino acid substitutions can be made to the native sequence without compromising its functional activity. Variations of these protein sequences contemplated for use in the present invention include minor insertions, deletions and substitutions. For example, conservative amino acid replacements are contemplated. Such replacements are, for example, those that take place within a family of amino acids that are related in the chemical nature of their side chains. The families of amino acids include the basic amino acids (lysine, arginine, histidine); the acidic amino acids (aspartic acid, glutamic acid); the non-polar amino acids (alanine, valine, leucine, isoleucine, proline, phenylalanine, methionine, tryptophan); and the uncharged polar amino acids (glycine, asparagine, glutamine, cysteine, serine, threonine, tyrosine) and the aromatic amino acids (phenylalanine, tryptophan, tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid, in an area outside of the polypeptide's active site, will not have a major effect on the properties of the polypeptide.

Figure 3:
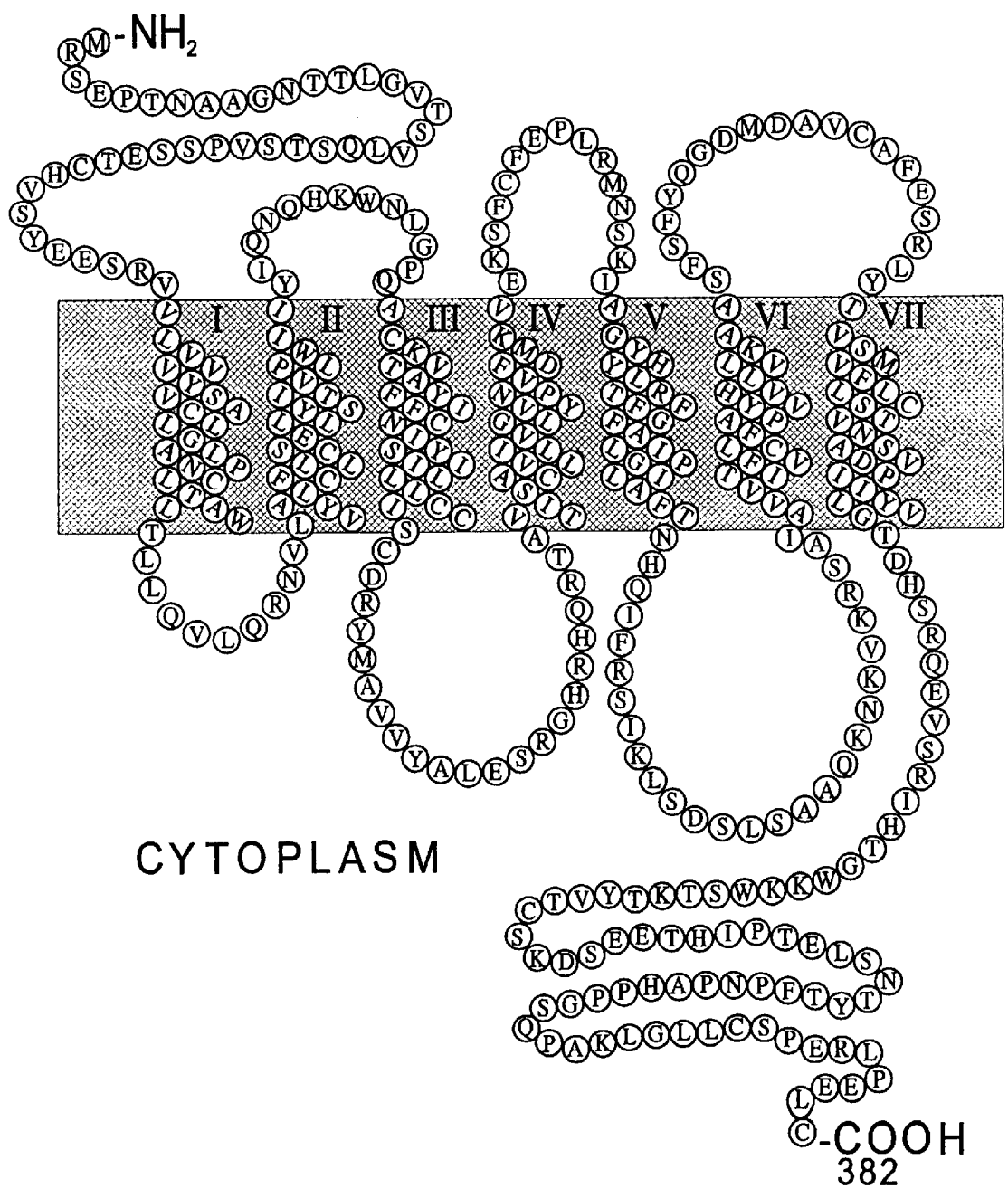
FIG. 3 is a schematic diagram of murine G2A (SEQ ID NO: 2) showing the seven predicted transmembrane domains.
Figure 4:
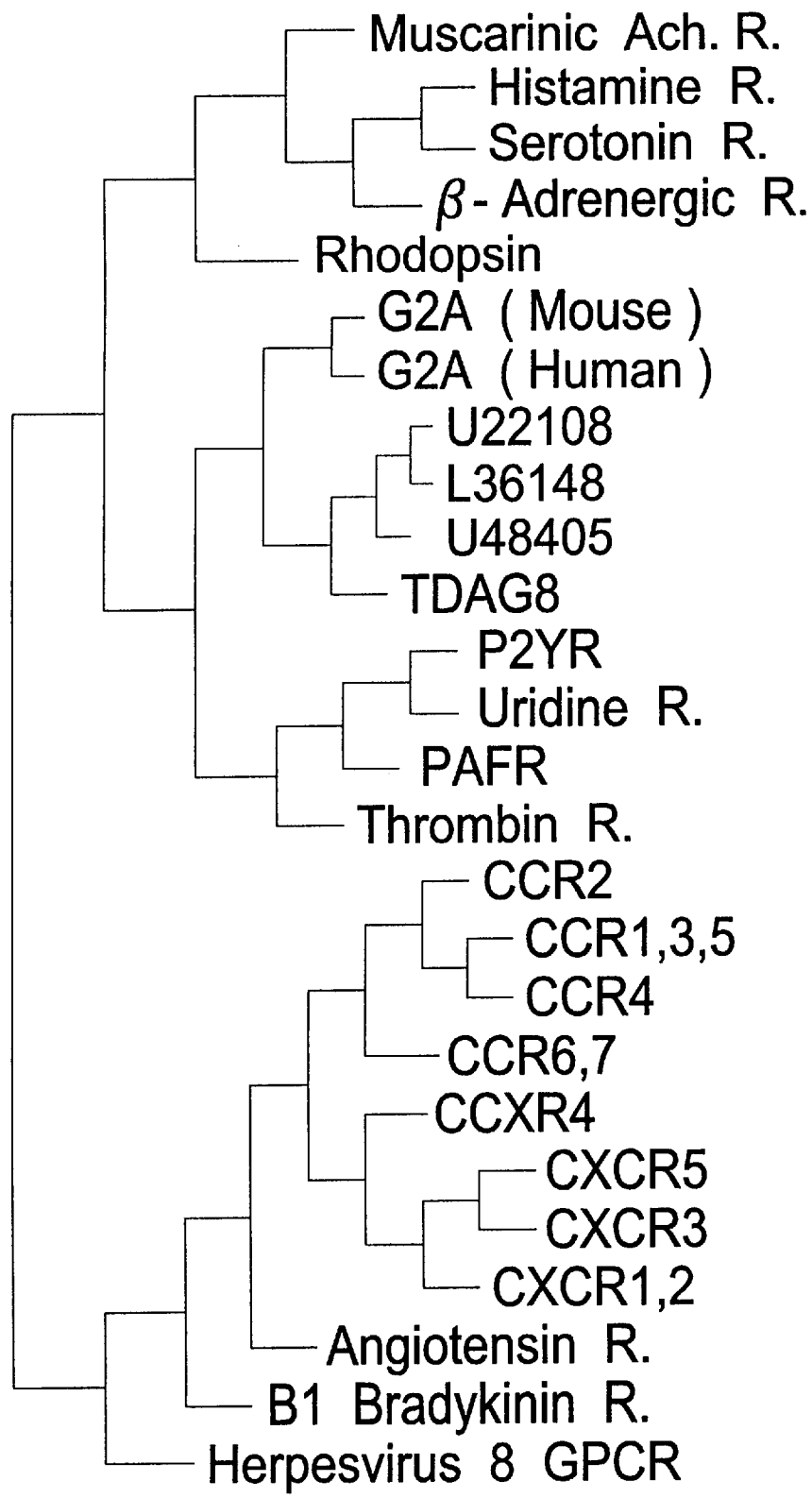
FIG. 4 is a phylogenetic tree of GPCRs showing the relationship of G2A with other GPCR family members.

The murine protein was determined to be a member of the GPCR superfamily by its homology to other GPCRs, including the mouse TDAG8 protein and the P2Y purinoceptor, using sequence alignment programs. A schematic diagram of murine G2A showing the seven predicted transmembrane domains is shown in FIG. 3. A GPCR phylogenetic tree is shown in FIG. 4. The human G2A homologue was isolated by screening a human spleen cDNA library under high stringency conditions (2×SSC, 0.1% SDS, 65° C.). The murine and human G2As share approximately 70% identity at the amino acid level (FIG. 5) and have a calculated molecular weight of about 42 kDa. These proteins share the highest degree of identity (76%) in the seven transmembrane domains as well as the extracellular and intracellular loops, whereas they are more divergent in the N-terminal extracellular domain (25% identity) and C-terminal cytoplasmic tail (55% identity). Both murine and human G2A contain putative N-linked glycosylation sites in the N-terminal extracellular domain characteristic of GPCRs. Any DNA molecule capable of hybridizing the DNA sequence shown in SEQ ID NO: 1 under these conditions or lower stringency conditions, as well as the protein encoded by such a DNA molecule, is within the scope of the invention.

Northern analysis of various murine tissue samples using a multiple tissue Northern blot detected two G2A transcripts of about 3 kb and 5 kb in hematopoietic tissues such as spleen, thymus, lung and heart, but not in normal bone marrow, brain, liver, skeletal muscle or kidney. Thymocytes were isolated and shown by a semi-quantitative RT-PCR to express G2A regardless of their developmental state. Northern analysis of human tissues showed that the human G2A is exclusively expressed in spleen and peripheral leukocytes, but not in heart, brain, placenta, lung, liver, skeletal muscle, kidney, pancreas, thymus, prostate, testis, ovary, small intestine and the mucosal lining of the colon. This further suggests a role of this gene in hematopoiesis. The human G2A is transcriptionally activated in B cells upon activation by either phorbol 12-myristate 13-acetate (PMA) plus ionomycin or anti-IgM antibodies. The activation of G2A transcription was also observed in B cells upon irradiation with x-rays or activation by the CD40 ligand. The human G2A transcript is also present in the ALL-1 and K-562 leukemia cell lines.

The G2A was transcriptionally activated by BCR-ABL and v-Abl, a protein tyrosine kinase oncogene found in Abelson Murine Leukemia Virus. To our knowledge, this is the first demonstration that a GPCR can be transcriptionally regulated by a protein tyrosine kinase. Interestingly, a mutant form of BCR-ABL (carrying a mutation in the SH2 domain) that lacks oncogenic potential failed to transcriptionally activate the G2A. In addition, Cyclin D1, an important cell cycle regulator (Afar et al., *Proc. Natl. Acad. Sci. U.S.A.* 92:9540–9544, 1995) that can complement the BCR-ABL mutant for transformation, restored the expression of the G2A. These data suggest that this GPCR may also be a marker for transformation by BCR-ABL and other tyrosine kinase signaling pathways.

Figure 6:
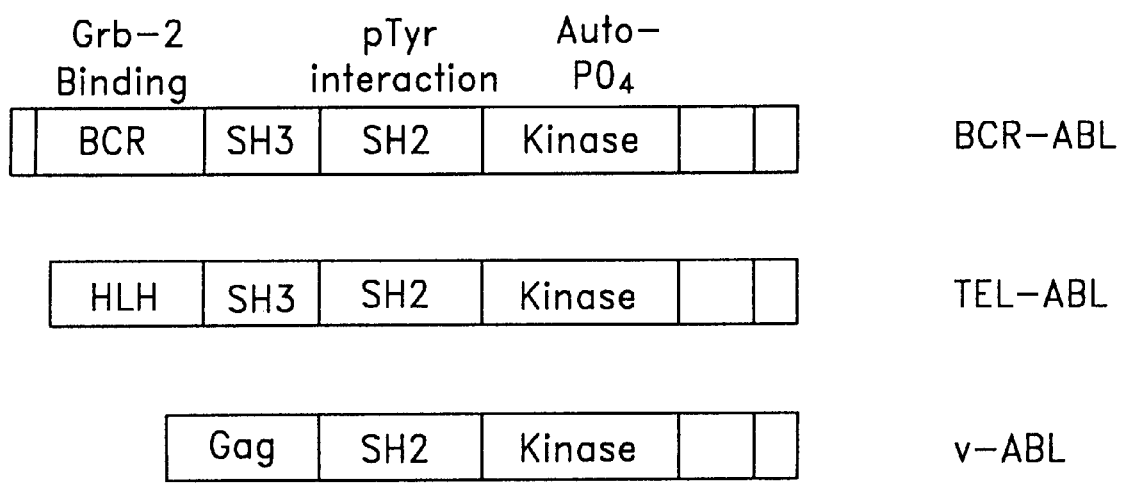
FIG. 6 is a schematic diagram showing the various domains of BCR-ABL, TEL-ABL and v-ABL. SH3=src homology region 3; SH2=src homology region 2; pTyr= phosphotyrosine; Auto-$PO_4$=autophosphorylation site; Grb-2=adaptor protein which couples BCR-ABL to Ras; HLH= helix-loop helix domain involved in oligomerization of the protein and activation of Abl kinase activity.

FIG. 6 shows the domains of BCR-ABL, TEL-ABL (an oncogenic fusion protein associated with leukemia) and v-ABL. TEL-ABL, Grb-2 (an adaptor protein which couples BCR-ABL to Ras) mutant and autophosphorylation mutant did not activate the G2A. The G2A receptor was also transcriptionally activated by v-Mos, a serine kinase oncogene that activates MAP kinase (Davis, *Mol. Reprod. Dev.* 42:459–67, 1995). Since v-Mos, BCR-ABL and v-ABL all activate MAP kinases (Davis, supra.), the G2A may be directly regulated by MAP kinase signaling pathways. Therefore, it is contemplated that the G2A may also be activated by a wide-variety of protein kinases as well as their regulators and effectors during cell growth and differentiation such as Ras, Myc, Fos, Jun and BTK.

The G2A is expressed in spleen and thymus, but not in normal bone marrow cells, suggesting that it may play an important role in mid- and late stages of T and B cell development. During development, self-reactive immature thymocytes are clonally deleted in the thymus, a phenomenon which establishes T cell tolerance (negative selection). It has been shown that the deletion of self-reactive immature T cells in the thymus is mediated by apoptosis upon T cell receptor engagement. TDAG8, a GPCR family member, is induced in T cells during apoptosis upon T cell receptor activation (Choi et al., *Cell. Immunol.*, 168:78–84, 1996). This suggests that TDAG8 may play a role in negative selection of T cells. Since the G2As that we isolated share about 30% homology with TDAG8, it is conceivable that the G2As may also play a role in negative selection of T cells. Sequence analysis of the G2A with its family members reveal that they also share significant homology with the P2Y receptor, a GPCR for ATP. It has been shown recently that P2Y receptor is transcriptionally upregulated during T cell activation (Koshiba et al., *Proc. Natl. Acad. Sci. USA.*, 94:831–836, 1997).

The G2As may play a role in directing migration of lymphocytes into specific anatomical compartments of spleen and thymus for maturation. Previous studies on a hematopoietic-specific GPCR, BLR1, suggest that BLR1 plays an important role for directing migration of lymphocytes into splenic follicles as well as migration of activated B cells into B cell-follicles of the spleen, a prerequisite for the development of an antigen-specific immune response (Forster et al., *Cell*, 87:1037–1047, 1996). Expression of G2As in hematopoietic-specific tissues suggest that it may also play similar roles in directing migration of lymphocytes into lymphoid organs for their maturation.

Both the mouse and human G2A cDNA clones can be used for in situ analysis to examine whether the expression of the receptor is restricted to certain anatomical regions of the spleen and thymus. The mouse and human genomic clones encoding the full length G2As were also isolated. The mouse genomic clone has been used for constructing a targeting vector to knock-out the G2A in mice by homologous recombination. The G2A-/-mice will allow further evaluation of the physiological functions of this receptor. The G2A-/-mice will also allow determination of whether in vivo leukemogenesis is dependent on the G2A. The mouse and human genomic clones may contain the distal and proximal promoters of the G2As that will allow the analysis of the transcriptional regulation of hematopoietic-specific genes. Both the mouse and human genomic clones can also be used for cytogenetic mapping to examine whether the G2As are linked to any known genetic diseases.

Rabbit antisera was prepared which was reactive with either the N-terminal portion or the C-terminal portion of the receptor as confirmed by ELISA. Two rabbits were injected with a 13 amino-acid peptide corresponding to the cytoplasmic tail of the receptor. Another two rabbits were injected with GST-G2A-N, a glutathione-S-transferase fusion protein containing the N-terminal extracellular domain of the G2A. The sera from the second, third, and fourth production bleed of both rabbits exhibited strong immune response to the peptide as seen in the ELISA assay. The antibodies were affinity purified using a peptide affinity column and are valuable for analyzing the expression of this G2A in T and B cell development. These antibodies were used to assist in determining the structure and localization of the G2A protein. The anti-N-terminal antibodies detected the G2A protein under the non-permeabilized and permeabilized conditions, whereas the anti-C-terminal antibodies only detected G2A under permeabilized conditions. These results suggest that the N-terminal portion is the extracellular domain and the C-terminal portion is the intracellular domain which is consistent with known GPCRs.

Monoclonal antibodies to the receptor can also be generated using conventional hybridoma technology known to one or ordinary skill in the art. Briefly, three mice are immunized with 25 $\mu$g recombinant receptor prepared as described in Example 9. Mice are inoculated at 3 week intervals with 20 $\mu$g G2A per mouse (½ subcutaneously and ½ intraperitoneally). Serum collected from each animal after the first inoculation reacts with G2A as determined by immunoprecipitation. Three days after the final inoculation, mice are sacrificed and the spleens harvested and prepared for cell fusion. Splenocytes are fused with Sp2/0 AG14 myeloma cells (ATCC CRL 1581) with polyethylene glycol (PEG). Following PEG fusion, cell preparations are distributed in 96-well plates at a density of $10^5$ cells per well and selected in hypoxanthine/aminopterinithymidine (HAT) medium containing 10% fetal calf serum and 100 U/ml interleukin-6. The medium is replaced with fresh HAT medium 10 days after plating. To identify hybridomas producing MAbs which recognize G2A, hybridoma supernatants are tested for the ability to immunoprecipitate purified recombinant G2A or to detect G2A by immunoblotting.

A glutathione-S-transferase (GST) fusion protein of the N-terminal extracellular domain of the G2A was constructed. The mouse and human G2As were cloned into various eukaryotic expression vectors which will allow the overexpression of recombinant mouse and human G2As in transfected cells in vitro and in vivo by methods well known to one of ordinary skill in the art. Preferably, the constructs containing the G2A is transfected into eukaryotic cells; more preferably into mammalian cells. Alternatively, the construct may be used to transform bacterial cells.

Growth arrest induced by G2A indicates its potential for therapeutic intervention in cases of deregulated proliferation of lymphoid cells. G2A resists cellular proliferation, thus its agonists are useful in delaying the progression of diseases including leukemias, lymphomas and autoimmune diseases. Since G2A is upregulated by BCR-ABL and can suppress the outgrowth of lymphocytes and fibroblasts (Tables 4A–B), antibodies, drugs or natural ligands can be screened in vitro which can activate G2A. Drugs, antibodies or natural ligands which inhibit the growth of lymphocytes are useful for treatment of the diseases mentioned above.

Conversely, monoclonal antibodies can be generated against particular regions of G2As which block the G2As and stimulate the growth of normal lymphocytes in vivo. In addition, in vitro screening assays can be used to find drugs or natural ligands which bind to and either activate or inactivate the G2A. These antibodies, drugs or natural ligands can stimulate the growth of lymphocytes, which may in turn cure or alleviate the symptoms of patients who have either inherited immunodeficiency diseases or Acquired immune deficiency syndrome (AIDS). For example, patients with severe combined immune deficiency (SCID), DiGeorge syndrome, or Bare lymphocyte syndrome lack T cells, and patients with X-linked agammaglobulinemia lack B cells. The antibodies, drugs, natural ligands can be delivered into these patients to inhibit the G2A to stimulate the growth of the T and B cells in their immune system.

In a preferred embodiment, the cDNA encoding the G2A is placed in a eukaryotic expression vector for transfection into or infection of a mammalian cell line. Many such cell lines are known in the art, including NIH 3T3, Rat-1, 293T, COS-1, COS-7 and Chinese hamster ovary (CHO) cells, most of which are available from the American type Culture Collection (ATCC), Rockville, Md. Many such expression vectors are known and are commercially available. Preferred expression vectors include retroviral vectors, adenoviral vectors and SV40-based vectors. The vector may contain a selectable marker, such as antibiotic resistance, to select for cells which are expressing the receptor. Alternatively, the expression of the G2A can be under the control of a regulatory promoter. Stable transfectants are used to screen large libraries of synthetic or natural compounds to identify compounds which bind to the G2A. Compounds which bind to the G2A are then tested in the assays described in Examples 7, 10, 11 and 12 to determine whether they are agonists or antagonists of BCR-ABL-mediated G2A activation.

In one embodiment of the invention, a compound to be tested is radioactively, colorimetrically or fluorimetrically labeled using methods well known in the art and incubated with the receptor. After incubation, it is determined whether the test compound is bound to the receptor. If so, the compound is a potential agonist or antagonist. Functional assays are performed to determine whether the receptor activity is activated or inhibited. These assays include fibroblast and bone marrow transformation assays, cell cycle analysis and in vivo tumor formation assay. Responses can also be measured in cells expressing the receptor using signal transduction systems including, but not limited to, protein phosphorylation, adenylate cyclase activity, phosphoinositide hydrolysis, guanylate cyclase activity, ion fluxes (i.e. calcium) and pH changes. These types of responses can either be present in the host cell or introduced into the host cell along with the receptor.

G2A receptor agonists isolated as described above can be used to promote cell cycle arrest at the G2/M transition in malignant cells, particularly hematopoietic cells such as leukemia cells and lymphoma cells, both in vitro and in vivo. Because G2A is induced by protein tyrosine kinase oncogenes, it can be used as a diagnostic marker for many types of cancer, including leukemia The DNA sequence can also be used as a probe to search for additional closely-related family members which may play similar roles in oncogenesis.

G2A is not expressed in normal bone marrow cells, but is expressed in spleen. Thus, it is possible that G2A regulates blood cell development. Regulation of the activity of the G2A (by antibodies, inhibitory or stimulatory drugs, or natural ligands) may be clinically useful in restoring the normal number and function of the blood cell population with suppressed hematopoiesis, such as that which occurs after treatment to obtain immune depression for organ transplants or after cytotoxic cancer therapy.

The expression of G2A in heart suggests that this gene may play a physiological role in heart. It has been shown that there are a variety of autoantibodies, including antireceptor autoantibodies, in patients with cardiomyopathy (Fu, Mol. Cell. Biochem. 163:343–7 (1996). Patients with cardiomyopathy may have autoantibodies against the G2A which contribute to the pathogenesis of cardiomyopathy. Therefore, regulation of G2A function by neutralizing antibodies, drugs, or natural ligands may alleviate the symptoms of patients with cardiomyopathy. The G2As may also be involved in cardiovascular, hypertension-related, cardiac function defects. Regulation of G2A function by neutralizing antibodies, drugs, or natural ligands may alleviate the symptoms in patients with such defects.

Since we have isolated both murine and human G2As, the cDNAs can be used to isolate the homologue of the G2As in other species. Identification of the homologues in other species may lead to a cure for the diseases mentioned above in animals, and will therefore have broad applications in veterinary medicine. The amino acid sequence information of the highly conserved regions of the murine and human G2As can be used to develop antibodies or drugs that can be used to treat diseases in both human and animals.

The following examples describe the cloning of the murine and human WT BCR-ABL-induced G2A.

EXAMPLE 1

Plasmid Constructs, Cell Lines, Preparation of Viral Stocks, Generation of Antibodies The WT p185 BCR-ABL and the SH2 mutant were cloned into the pSRαMSV vector (Muller et al., Mol. Cell. Biol. 11:1785–1792. 1991) under the control of the LTR promoter as previously described (Afar et al., Science 264:424–426, 1994; Pendergast et al., Cell 75:175–185, 1993). The pSRαMSV vector was used to produce helper-free retroviral stocks by transient transfection of 293T cells along with the Ψ⁻ packaging vector (Pear et al., Proc. Natl. Acad. Sci. U.S.A., 90:8392–8396, 1993; Afar et al., Science 264:424426, 1994). A 13-amino acid peptide (KDSEETHLPTELS; SEQ ID NO: 5) corresponding to the C-terminal intracellular portion of the murine G2A was synthesized and injected into rabbit for antibody production (Babco, Berkeley, Calif.). Five production bleeds were obtained. To generate the antibodies against the murine N-terminal extracellular portion of the G2A, a GST-Mu-G2A-N fusion construct was made by PCR using GST-Mu-N2A-N5' and GST-Mu-N2A-N3' primers (See Table 2).

Briefly, PCR was performed in a total of 100 μl reaction mixture containing 20 ng template, 30 μl 3.3X XL buffer (Perkin Elmer, Norwalk, CT), 6 μl 25 mM magnesium acetate, 2 μl dNTPs (10 mM each nucleotide), 20 pmol of GST-Mu-N2A-N5' and GST-Mu-N2A-N3' primers, and 1 μl rTth polymerase (Perkin Elmer). The cycling conditions were 95° C. for 5 min, 30 cycles of denaturation at 94° C. for 0.5 min, annealing at 56° C. for 1 min and elongation at 72° C. for 1 min. After incubation at 72° C. for 10 min, the amplified PCR fragment was digested with BamHI and EcoRI (Boehringer Mannheim, Indianapolis, Ind.) in Buffer B (10 mM Tris, 5 mM $MgCl_2$, 100 mM NaCl, 1 mM P-mercaptoethanol, pH 8.0, Boehringer Mannheim), and fractionated on an agarose gel. The DNA fragment was excised, purified using Geneclean™ (Bio 101, La Jolla, Calif.) and cloned into the pGEX-2T vector (Pharmacia Biotech) at the BamHI/EcoRI sites. Approximately 50 ng pGEX-2T BamHi/EcoRI fragment was ligated to the PCR product at a 1:3 molar ratio in 1X T4 DNA ligase buffer (50 mM Tris-HCl (pH 7.8), 10 mM $MgCl_2$, 10 mM DTT, 1 mM ATP, 50 µg/ml BSA) and 1 µl T4 DNA ligase (New England Biolabs, Beverly, Mass.) in a 10 µl reaction volume at 16° C. overnight. Transformation was performed by mixing 10% of the ligation reaction with 100 µl of DH5 α competent *E. coli* cells on ice for 20 min. After heat shock at 42° C. for 2 min and incubation on ice for 2 min, 1 ml TYE was added and the transformed cells were further incubated at 37° C. for 1 hr. The transformation mix was plated out on TYE plates containing ampicillin (50 µg/ml). One positive clone containing the insert was identified. The plasmid was sequenced to ensure the proper fusion of the murine N-terminal extracellular portion of G2A to GST.

EXAMPLE 2

Isolation of cDNA from Bone Marrow Cells

Total RNA was isolated from primary murine bone marrow cells transformed by a retrievers encoding either the WT p185 BCR-ABL or the SH2 mutant variant (Goga et al., *Cell* 82:981–988, 1995) using the Ultraspec RNA isolation system (Biotecx Laboratories, Inc., Houston, Tex.). Polyadenylated RNA was purified from total RNA using oligo (dT) cellulose columns (Collaborative Research) according to the manufacturer's instructions. cDNA was synthesized using SuperScript choice system (GibcoBRL Life Technologies, Gaithersburg, Md.), according to the manufacturer's protocols.

EXAMPLE 3

Representational Difference Analysis (RDA) and DNA Sequencing

To isolate genes that were differentially regulated by the WT p185 BCR-ABL, but not by the SH2 mutant variant, a modified version of a PCR-based subtractive-hybridization technique called Representational Difference Analysis (RDA) was used. RDA was originally developed to detect differences between two complex genomes (Lisitsyn et al., *Science*, 259:946–951, 1993). It was later adapted for use with cDNA and has been used successfully to isolate differentially expressed genes in various systems (Hubank et al., *Nucl. Acids Res.* 22:5640–5648, 1994; Braun et al., *Mol. Cell. Biol.* 15:4623–4630 (1995). The cDNA sample containing the genes of interest is termed the tester, and the sample used for subtraction is the driver. Both the tester and driver cDNAs are digested with a restriction enzyme, DpnII, then ligated to RBgl adapters (the RBgl12 and RBgl24 primers, see Table 2) for PCR amplification. The RBgl adapters were then removed. To isolate differentially-expressed genes, the amplified tester DNA is ligated to new adapters, JBgl adapters (the JBgl 12 and JBgl 24 primers, see Table 1) and mixed with the driver DNA in a subtractive hybridization. The differentially-expressed genes form tester-tester homo-duplexes and can be preferentially amplified by PCR using the JBgl24 primer. This process is repeated three times, with increasing ratios of driver to tester from 1:100, 1:800, to 1:8000 during subtractive hybridization (Lisitsyn et al., supra.; Hubank et al., supra.).

In this study, cDNA from HDBM cells transformed by the WT p185 was used as the tester and that by the SH2 mutant as the driver to isolate genes that are upregulated by the WT p185 BCR-ABL. RDA was also performed in parallel using the SH2 mutant as the tester and the WT as the driver to isolate genes that are downregulated by the WT p185. The differentially amplified gene fragments were then digested with DpnII and cloned into the BamHI site of the pBluescript cloning vector (Stratagene, La Jolla, Calif.). DNA sequencing was then performed using ABI PRISM Dye Terminator Cycle Sequencing Ready Reaction Kit (Perkin Elmer) or Sequenase version 2.0 DNA sequencing kit (United States Biochemical, Cleveland, Ohio). After sequencing the clones from both directions, the sequence information was used to search databases using the BLAST program. Both the protein database (non-redundant updated protein database PDB+SwissProt+PIR) and nucleotide database (PDB+GenBank+EMBL) were searched. Sequence analysis of a 377 base-pair DNA fragment of a partial murine G2A clone (N2A) revealed that it was a novel G2A homologous to multiple GPCR family members in the database.

TABLE 1

| Oligonucleotides used for RDA | |
|---|---|
| RBgl24 | AGCACTCTCCAGCCTCTCACCGCA (SEQ ID NO: 6) |
| JBgl24 | ACCGACGTCGACTATCCATGAACA (SBQ ID NO: 7) |
| NBgl24 | AGGCAACTGTGCTATCCGAGGGAA (SEQ ID NO: 8) |
| RBgl12 | GATCTGCGGTGA (SBQ ID NO: 9) |
| JBgl12 | GATCTGTTCATG (SEQ ID NO: 10) |
| NBgl12 | GATCTTCCCTCG (SEQ ID NO: 11) |

EXAMPLE 4

Isolation of Mouse G2A cDNA and Genomic Clones

The 377 bp N2A fragment was used as a probe to screen a mouse spleen cDNA library (Clontech, Palo Alto, Calif.) according to the manufacturer's instructions. Briefly, *E. coli* strain 1090r- was grown in TYE broth in the presence of 10 mM $MgSO_4$ and 0.2% maltose overnight. The library was incubated with overnight *E. coli* culture and then plated out on TYE plates using 0.7% agarose in TYE+20 mM $MgSO_4$. After incubation at 37° C. until plaques were about 1 mm in diameter, the plates were chilled at 4° C. for 1 hr before the filters were placed on the plates. The filters were then lifted and autoclaved at 100° C. for 1 min to denature the DNA. The filters were prehybridized for 4 h in hybridization buffer containing 1% SDS, 2X SSC (20X SSC=3 M NaCl, 0.3 M NaCitrate-2 $H_2O$, pH to 7.0), 10% dextran sulfate, 50% formamide, 1 X Denhardt's solution (50 X Denhardt's solution=1% ficoll, 1% polyvinylpyrrolidone and 1% BSA, pentax fraction V) and 0.25 mg/ml salmon sperm DNA. The N2A fragment was labeled using Primer-It II Random Primer Labeling Kit (Stratagene). The filters were hybridized overnight at 42° C. with the N2A probe in the hybridization buffer. The filters were washed twice with 2X SSC and 0.1% SDS for a total of 1.5 hrs. One positive clone was identified after screening $1 \times 10^6$ plaques. Sequence analysis revealed that the clone contained the C-terminal portion of the G2A. 5'-RACE was then used to obtain the N-terminal portion of the gene using 5' RACE system (GibcoBRL) according to the manufacturer's instruction. Briefly, the N2AGSP1 primer (see Table 2) was used to prime first-strand cDNA synthesis. After purification of first-strand cDNA and homopolymer addition of dCTP by terminal deoxynucleotidyl transferase (TdT) to the cDNA at the 3' end, a nested primer, N2AGSP2 (see Table 2) that anneals to sequences located 3' of N2AGSP1 and the 5' RACE anchor primer (see Table 2) were used for PCR amplification of the N-terminal fragment of the murine G2A. The PCR was performed in a 50 µl reaction mixture containing 20 mM Tris-HCl (pH 8.4), 50 mM KCl, 1.5 mM MgCl2, 200 uM each dNTP, 100 nM N2AGSP2 primer and 100 nM anchor primer. The dC-tailed cDNA was first denatured at 94° C. for 5 min. After addition of 2 units Taq DNA polymerase, PCR was performed by 35 cycles of denaturation at 94° C. for 0.5 min, annealing at 62° C. for 1 min and elongation at 72° C. for 3 min.

After obtaining the sequence information of the N-terminal portion of the gene, a full length clone was obtained by RT-PCR (3'RACE system, GibcoBRL) using total RNA isolated from bone marrow cells transformed by the WT BCR-ABL. The primers for generation of full length murine G2A were N2A 3' RACE-1 (5' primer) and MuN2A3'-2 (3' primer) (see Table 2). Briefly, PCR was performed in a 50 µl reaction mixture using the rTth DNA polymerase system (Perkin Elmer) containing 1X XL buffer, 1.5 mM magnesium acetate, 10 pmol of each primer, 2 µl of first strand cDNA synthesis product, 0.2 mM dNTPs and 0.5 µl of rTth polymerase (Perkin Elmer). The cycling conditions were 94° C. for 3 min, 35 cycles of denaturation at 94° C. for 0.5 min, annealing at 62° C. for 1 min and elongation at 72° C. for 3 min. The amplified PCR fragments were fractionated on an agarose gel. The approximately 1.3 kb fragment containing the fill length murine G2A cDNA (SEQ ID NO: 1) was excised, purified using Geneclean™ and subcloned into the pCRII vector (Invitrogen, San Diego, Calif.). Multiple clones were sequenced using N2AGSP2, N2Arandom, N2A5, T7, and M13 Reverse primers (see Table 2). To create a hemagglutinin (HA)-tag version of murine G2A, PCR was performed using the MuN2A-HA-N and MuN2A-HA-C primers (see Table 2). The amplified PCR fragment was subcloned into the pCRII vector (Invitrogen). The insert was then excised with XhoI and NotI and subcloned into the pGD retroviral expression vector at the XhoI and NotI site. Multiple PCR clones were sequenced from both directions to ensure the in-frame fusion of the G2A with the HA-tag engineered at the NotI site of the pGD expression vector.

To obtain the mouse G2A genomic clone, the mouse G2A cDNA was used as a probe to screen a mouse genomic library. The library was made with genomic DNA from mouse strain 129. The genomic DNA was partially digested with MboI, size-fractionated (17–21 kb), and ligated into the BamHi site of DashII arms (Stratagene). At least one positive clone was isolated and the authenticity of the clone was verified by direct sequencing of the genomic DNA and by PCR analysis using primers specific for the gene.

TABLE 2

Oligonucleotides used in the analysis of Murine G2A

| Primer | Sequence, 5'-3' |
| --- | --- |
| MuN2A3'RACE-1 | CAGGACTGGCTTGGGTCATT (SEQ ID NO: 12) |
| MuN2A3'RACE-2 | GTCCACAGAACTCACATAGGA (SEQ ID NO: 13) |
| MuN2A3'-1 | CGCGGATCCGAATTCGGTACCGGTGACTCAGAGGACCAG (SEQ ID NO: 14) |
| MuN2A-HA-N | CGGAATTCTCGAGTCAGGACTGGCTTGGGTCATT (SEQ ID NO: 15) |
| MuN2A-HA-C | ATAGTTTAGCGGCCGCGCAGAGCTCCTCAGGCAGT (SEQ ID NO: 16) |
| Mu + HuN2A + 8 | CAAGAAGTGTCCAGAATCCA (SEQ ID NO: 17) |
| N2AGSP1 | GGTGACAGCAGTCCTCTGGT (SEQ ID NO: 18) |
| N2AGSP2 | TAGCGGTCGCAGGAAATGCAG (SEQ ID NO: 19) |
| N2Arandom | TGATTGGTGAACGCCAGG (SEQ ID NO: 20) |
| N2A5 | GCTTTGAGCCCCTGAGGATGAA (SEQ ID NO: 21) |
| T7 | GTAATACGACTCACTATAGGGC (SEQ ID NO: 22) |
| GST-Mu-N2A-N5' | GTCGGATCCATGAGATCAGAACCTACCAAT (SEQ ID NO: 23) |
| GST-Mu-N2A-N3' | GTCGAATTCTCACAGGACCACTCTGCTCTC (SEQ ID NO: 24) |
| M13 Reverse | CAGGAAACAGCTATGAC (SEQ ID NO: 25) |
| Anchor Primer | CUACUACUACUAGGCCACGCGTCGACTAGTACGGGIIGGGIIGGGIIG (SEQ ID NO: 26) |
| MuN2A3'HA | GCCGAATTCTCAAACTCCGGC (SEQ ID NO: 27) |
| MuN2Aflag5 | CCGGAATTCGGCCACCATGGACTACAAGGACGACGATGACAAGAGATCAGAACCTACCAATGCA (SEQ ID NO: 28) |
| MuN2A5'Eco | CCGGAATTCCTAGAGGCCACCATGAGATCAGAACCTACCAAT (SEQ ID NO: 29) |

EXAMPLE 5

Isolation of Human G2A cDNA and Genomic Clones

The murine G2A was used as a probe to screen a human spleen cDNA library (ClonTech, Palo Alto, Calif.) to isolate the human homologue. The probe was labeled as described above. The hybridization was performed in Rapid-hyb buffer (Amersham Life Science, Arlington Heights, Ill.) for 2 hrs at 65° C. The filters were washed twice with 2X SSC and 0.1% SDS at 65° C. for a total of 40 mins. At least four positive clones were isolated after screening $1.5 \times 10^6$ plaques. Sequence analysis revealed that these were overlapping clones containing an open reading frame encoding a protein of 380 amino acids with a calculated molecular weight of 42 kD. Multiple clones were sequenced from both directions to ensure the accuracy of the sequence. PCR was then used to amplify the full length human G2A from the human spleen cDNA library using the gene-specific primers HuN2A+ N1HA (5'primer) and HuN2A-C (3' primer) (see Table 3). To generate a HA-tag version of human G2A, the 5' primer HuN2A+N1HA and 3' primer HuN2A-HA-C were used (see Table 3). The amplified PCR fragment containing the full length human G2A cDNA (SEQ ID N: 3) was purified using Geneclean™ and cloned into the pCRII vector. Multiple clones were sequenced using T7, SP6, N2AGSP2, Mu+HuN2A+8, HuN2AE+2A, HuN2AC-8, and HuN2A+6 primers (Table 2) to ensure the accuracy of the sequence. Alignment of the mouse and human G2As show that they are about 70% identical to each other at the amino acid level.

TABLE 3

Oligonucleotides used in the analysis of human G2A

| Primer | Sequence, 5'-3' |
|---|---|
| HuN2A+N1HA | CGCTCGAGTGGGAGCAAATGCGGAGCGAG (SEQ ID NO: 30) |
| HuN2A-C | TTAGCGGCCGCTCAGCAGGACTCCTCAATCAG (SEQ ID NO: 31) |
| Hun2A-HA-C | TTAGCGGCCGCGCAGGACTCCTCAATCAGCCTC (SEQ ID NO: 32) |
| Mu+HuN2A+8 | CAAGAAGTGTCCAGAATCCA (SEQ ID NO: 33) |
| HuN2A+9 | ACCAGCCACAGTGCCCATG (SEQ ID NO: 34) |
| HuN2AE+2A | TGCCACTCTGGGTCATCTAT (SBQ ID NO: 35) |
| HuN2A+6 | CGGTGGTTGTCATCTTCCTA (SEQ ID NO: 36) |
| T7 | GTAATACGACTCACTATAGGGC (SEQ ID NO: 37) |
| M13 Reverse | CAGGAAACAGCTATGAC (SEQ ID NO: 38) |

EXAMPLE 6

Northern analysis

RNA was purified using the Ultraspec RNA isolation system (Biotecx laboratories, Inc., Houston, Tex.). To examine the expression level of a gene of interest, a DNA fragment of the gene was labeled using the Prime-it II random primer labeling kit (Stratagene). Northern blotting was performed as previously described (Schneider at al., Cell 54:787–793, 1993). Briefly, the RNA samples were fractionated in an agarose gel (1% agarose, 20 mM phosphate, pH 7.0, 7% formaldehyde), transferred to Nitro-Pure nitrocellulose transfer membrane (Micron Separations, Inc. Westborough, Mass.) using 20 X SSC. The blot was baked at 80° C. for 2 h and prehybridized in the prehybridization buffer (50% formamide, 5 X SSC, 1X Denhardt's, 50 mM phosphate stock buffer and 0.25 mg/ml salmon sperm DNA) for 4 h. The blot was then hybridized overnight at 42° C. with the probe in 8 ml prehybridization buffer and 2 ml 50% dextran sulfate. The blot was washed once with 2X SSC, 0.1% SDS at room temperature for 30 min, and once with 2X SSC, 0.1% SDS at 60° C. for 30 min. The blot was exposed to x-ray film at −70° C.

To assess whether G2A affects hematopoietic cell transformation by BCR-ABL, a bone marrow transformation assay was applied to quantitively measure the kinetics of the BCR-ABL-mediated transformation in the presence or absence of G2A. Retroviral-mediated expression of BCR-ABL in primary murine bone marrow cells results in the outgrowth of stromal cell-dependent pre-B cultures (McLaughlin et al., 1987). The growth rate of pre-B cells from infected marrow is directly dependent on the strength of the tyrosine kinase activity. To monitor the protein level of ectopically-expressed G2A, a chimeric G2A-GFP fusion protein was generated whose level could be quantitatively measured by FACS. The assay was performed as described in the following example.

EXAMPLE 7

Murine Bone Marrow Transformation Assay and Reconstitution of Irradiated Mice

Fresh bone marrow cells from the tibias and femurs of 3- to 4-week-old BALB/c mice were isolated and infected with retrovirus encoding either the WT BCR-ABL p185 along with the G2A-GFP fusion protein (PMSCV G2A-GFP IRES p185 WT) or GFP as a control. IRES is an internal ribosome entry binding site element which improves the yield of the expressing clones. The anti-sense version of G2A-GFP and GFP were also used as controls. The cells were plated at a density of $5 \times 10^6$ cells per 6-cm dish in RPMI containing 10% fetal bovine serum and β-mercaptoethanol ($5 \times 10^{-5}$ M) as previously described (McLaughlin et al., Mol. Cell. Biol. 9:1866–1874, 1989). The viral stocks were prepared as described (Goga et al., Cell 82:981–988, 1995). Liquid cultures were plated in triplicates and monitored for pre-B cell growth. Transformed pre-B-lymphoid cells were counted at various days following infection. The Expression of G2A-GFP and GFP were confirmed by FACS analysis.

Figure 7:
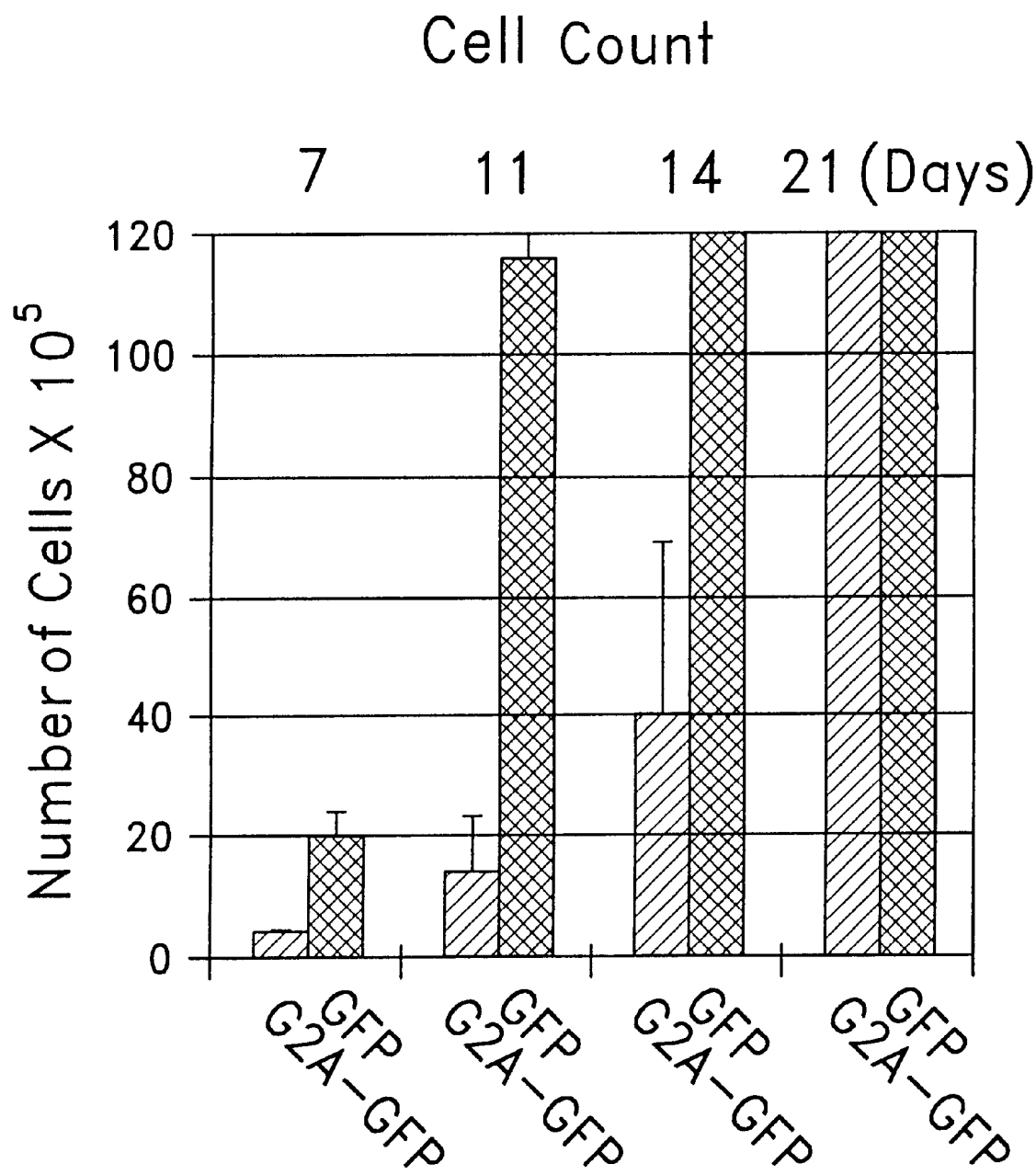
FIG. 7 shows the effect of G2A on the growth of bone marrow cells transfected with a retroviral vector encoding BCR-ABL and G2A-GFP or BCR-ABL and GFP (control).

During the first two weeks of the assay, G2A expression with BCR-ABL delayed the induction of pre-B cell outgrowth compared to BCR-ABL plus GFP or the G2A-GFP anti-sense control. Bone marrow cultures transformed by BCR-ABL in the absence of G2A reached confluency (>$1 \times 10^7$ cells per 3 ml culture) within 1½ weeks, whereas it took nearly three weeks to reach saturation in the presence of G2A (FIG. 7). Similar results were obtained in three independent experiments. This indicates that G2A slows the transformation process of BCR-ABL in lymphoid cells. Because G2A is linked to GFP, protein levels could be measured in these cultures during the three-week period by FACS. GFP alone did not significantly change its expression levels; however, G2A-GFP protein levels decreased gradually and after three weeks were nearly undetectable (FIG. 8). This counter-selection against B cells expressing high levels of G2A strongly suggests an anti-oncogenic effect of G2A as seen in fibroblasts.

Since G2A is not natively expressed but induced by BCR-ABL in pre-B cells, it was determined whether the expression of G2A was regulated during different states of B cell development. B lymphocytes are generated from hematopoietic stem cells by successive steps of differentiation during which a diverse repertoire of antigen receptors are generated by immunoglobulin gene rearrangement. The initiation of D–J rearrangement occurs in the early pro-B cells and at the pre-B cell stage, intact heavy chains are produced. The light chain genes then undergo rearrangement resulting in the expression of a complete IgM protein on the surface of immature B cells which then differentiate into IgM and IgD-expressing mature B cells capable of responding to antigen.

EXAMPLE 7A

Transcriptional Regulation of G2A in B Cells

To examine the expression of G2A, mouse bone marrow B cells were fractionated into pro-B, pre-B, immature B and mature B cells to examine the expression of G2A in different developmental compartments in lymphoid cells. A semi-quantitative RT-PCR method was used to measure the RNA levels of G2A. The G2A transcript is almost exclusively present in pro-B cells which coincidentally have the highest proliferation potential and are undergoing recombination. Extended PCR cycles revealed a low level of G2A transcript in pre-B and immature B cells.

Figure 9:
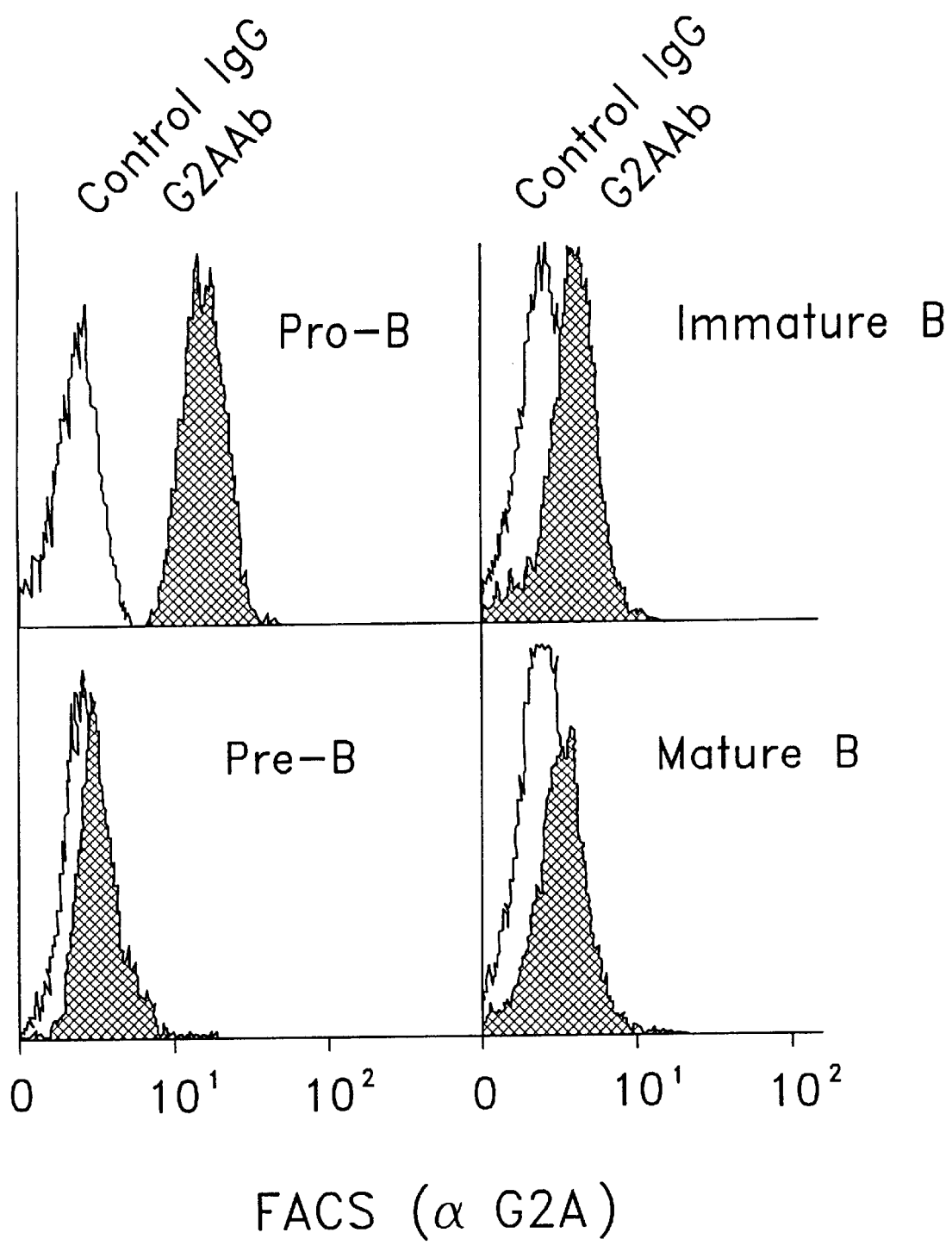
FIG. 9 is a flow cytometry profile showing the expression of G2A in pro-B, pre-B, immature B and mature B cells.

Rabbit polyclonal anti-G2A antibodies were used to examine the protein level of G2A in the same pro-B, pre-B, immature B and mature B cell fractions. High levels of G2A protein were detected in pro-B cells whereas very weak staining was present in the other three fractions of B cells using FACS (FIG. 9). These results show that the mRNA level of G2A corresponds to G2A protein level and that the effect of G2A may be predominantly restricted in pro-B cells.

To determine whether natural stimuli could activate G2A in more mature B cells, we used a human B cell line (Ramos) as a model system in which G2A expression is at a basal level. Ramos cells (and Jurkat cells, a human T cell line) were activated by anti-IgM antibodies to examine whether activation of B cell receptors (BCR) induced G2A transcription.

EXAMPLE 8

Regulation of G2A Transcription During B and T Cell Activation

Human B cells (Ramos) and T cells (Jurkat) were grown in RPMI 1640 containing 10% fetal calf serum to a density of $2 \times 10^6$ cells/ml. The cells were resuspended at a density of $2 \times 10^8$ cells/ml in serum-free RPMI immediately prior to stimulation. For activation of Ramos cells with anti-IgM, goat anti-IgM was added to cell suspensions (0.5 ml) at a final concentration of 10 µg/ml. After 0 min, 5 min, 7 hours and 24 hours at 37° C., RNA was isolated.

For activation of Ramos and Jurkat cells with ionomycin and PMA, ionomycin and PMA were added to the cells to a final concentration of 2 µg/ml and 20 ng/ml, respectively, and RNA was isolated at 0, 3, 6, 24 and 48 hours. For activation of Jurkat cells by anti-CD3 and CD28 antibodies, respectively, each 10 cm plate was coated with anti-CD3 (6.25 µg) and anti-CD28 (12.5 µg) antibodies (Sigma, St. Louis, Mo.). The Jurkat cells were subsequently seeded onto the antibody-coated plates. The cells were harvested at 0, 3, 6, 24 and 48 hours after activation and RNA was isolated.

For RT-PCR, 5 µg total RNA from each sample was used to synthesize the first strand cDNA using the Superscripts preamplification system (GIBCO BRL). Ten percent of the first strand cDNA synthesis product was then used for PCR. The HuN2A-C1 (SEQ ID NO: 28) and HuN2A+6 (SEQ ID NO: 33) primers were used for amplification of the human G2A fragment. A control set of primers, G3PDH control amplimers set for human and mouse (5'-ACCACAGTCCATGCCATCAC-3'; SEQ ID NO: 39 and 5'-TCCACCACCCTGTTGCTGTA; SEQ ID NO: 40), were used to ensure that equal amounts of template were used. PCR was performed in a 50 µl reaction mixture containing 1×PCR buffer (20 mM Tris-HCl, pH 8.4, 50 mM KCl; GIBCO), 1.5 mM $MgC_2$, 0.4 mM of each dNTP, 10 pmol of each primer, 0.5 µl Taq DNA polymerase (GIBCO) and 2 µl of first strand cDNA synthesis product. The cDNA was denatured at 94° C. for three minutes. PCR was performed by 35 cycles of denaturation at 94° C. for 0.5 min, annealing at 58° C. for 1 min, and elongation at 72° C. for 2 min.

The G2A transcript was barely detectable in unstimulated Ramos cells. The human G2A was found to be transcriptionally upregulated in B cells within 4 hours of activation by anti-IgM antibody, suggesting that strong B cell receptor crosslinking regulates the expression of G2A. Upregulation of the G2A transcript was also observed in response to receptor-independent activation of intracellular signaling pathways. The simultaneous addition of ionomycin and PMA to B cells to increase the intracellular calcium levels and to activate Protein Kinase C, respectively, resulted in increased levels of G2A mRNA. Time course analysis of the G2A transcript demonstrated that induction required between 2 and 4 hours with these activators. Activation of Ramos cells with CD40 ligand also upregulated the G2A transcript. In addition, exposure of Ramos cells to x-ray irradiation, a process which induces DNA damage and cell cycle arrest, also induced the transcription of G2A. However, no dramatic alteration in G2A transcript levels was observed in Jurkat cells upon activation by PMA plus ionomycin or anti-CD3 plus CD28 antibodies. These data suggest that the human G2A may play a role during B cell activation. As a control, glyceraldehyde 3-phosphate dehydrogenase (G3PDH) control amplimer set was used to ensure that equal amounts of templates were used for RT-PCR. Taken together, these results suggest that the G2A may play a role upon B cell activation. The transcriptional activation of G2A may either be involved in apoptosis of B cells or proliferation and/or differentiation of B cells.

It has been shown that transcription of the tumor suppressor gene p53 can be induced by ionizing radiation. Since G2A functions like a tumor suppressor gene and its expression is transcriptionally regulated by various stimuli, it was determined whether DNA damaging agents which activate many of the tumor suppressor genes could also induce the expression of G2A.

EXAMPLE 8A

Induction of G2A Expression by DNA-Damaging Agents

Varying doses of X-rays were used to irradiate Ramos cells and total RNA samples were extracted after overnight incubation. The G2A transcript was induced in a dosage dependent manner and reached a maximum at about 9 Gy. Since ionizing radiation causes single and double strand DNA breaks, it was also determined whether other DNA-damaging agents could also activate G2A transcription. A broad range of agents were chosen which may cause different types of DNA lesions: UV irradiation which induces the formation of thymidine dimers; chemical agents which inhibit de novo DNA precursor synthesis (hydroxyurea, 5-fluorouracil); chemical agents which directly block DNA synthesis (cytosine arabinoside, taxol, etoposide); or agents which intercalate into the DNA double helix (doxorubicin). The G2A transcript was found to be upregulated in response to all of the DNA damaging agents tested, suggesting that the induction of G2A may be due to activation of a general sensor of DNA damage.

EXAMPLE 9

Insertion of Mouse and Human G2As Into Expression Vectors

G2A cDNA was inserted into several eukaryotic expression vectors. Any of these constructs can be used to transfect eukaryotic cells, preferably mammalian cells, for production of recombinant G2A using methods well known in the art. Such methods are described in, for example, Sambrook et al. (*Molecular Biology: a Laboratory Manual*, Cold Spring Harbor Laboratory, 1988; Ausubel, *Current Protocols in Molecular Biology*, 1989). Such eukaryotic cells include Rat-1, NIH 3T3, 293T, CHO, COS-7 and BHK cells. The G2A can also be inserted into a baculovirus expression vector which is used to infect Sf9 insect cells using methods well known in the art.

N-terminal flag-tagged mouse G2A in the pCRII vector (Invitrogen) was used for in vitro transcription and translation of mouse G2A and for making probes for Northern, S1 or in situ analysis. Reverse transcription of RNA into first strand cDNA was performed using RNA isolated from bone marrow cells transformed with WT BCR-ABL. PCR was performed using 10 pmol of MuN2Aflag5 and MuN2A3'-1 primers (Table 2) in 50 μl reaction mixture containing 1 X pfu buffer (20 mM Tris-HCl, pH 8.75, 10 mM KCl, 10 mM $(NH_4)_2SO_4$, 2 mM $MgSO_4$, 0.1% Triton X-100, 100 μg/ml BSA) (Sigma). The cDNA was first denatured at 94° C. for 3 min. PCR was performed by 35 cycles of denaturation at 94° C. for 0.5 min., annealing at 62° C. for 1 min. and elongation at 75° C. for 3 min. The amplified PCR product was cloned into the pCRII vector (Invitrogen) according to the manufacturer's instructions.

The pSRα-Flag-G2A tk Neo expression vector is a retroviral expression vector for expression of mouse and human G2As in mammalian cells. In this construct, the Neo gene is under control of the herpes simplex virus thymidine kinase (tk) promoter for selection of infected cells with G418. The EcoRI insert from pCRII-Flag-Mu-G2A was excised and cloned into pSRα-Flag-G2A tk Neo at the EcoRI cloning site upstream of the TK promoter.

pCRII-Mu-G2A, the untagged version of pCR-Flag-Mu-G2A, was used for in vitro transcription and translation, and for making probes for Northern, S1 or in situ analysis. For construction of this vector, RT-PCR was performed using primers MuN2A5'Eco and MuN2A3'-I (Table 2) using the protocol described for pCRII-Mu-G2A. The amplified PCR product was cloned into the PCRII vector. In vitro transcription and translation were performed using the TNT-coupled reticulocyte lysate system (Promega, Madison, Wis.) according to the manufacturer's instructions. The in vitro transcription and translation of Mu-G2A revealed a protein product having a molecular weight of about 42 kDa which is similar to the calculated molecular weight of mouse G2A.

pCRII-Mu-G2A-HA, the C-terminal HA-tagged version of mouse G2A was used for in vitro transcription/translation and for labeling proves for Northern, S1 or in situ analysis. For construction of this vector, RT-PCR was performed using primers MuN2A5'Eco and MuN2A3'HA using the plasmid vector pGD-Mu-G2A-HA containing the HA-tagged version of murine G2A. The PCR product was cloned into the PCRII vector (Invitrogen).

For construction of pMu-G2A-GFP, the mouse G2A was fused to the N-terminal green fluorescence protein (GFP) in the pEGFP-N1 vector (Clontech). The murine G2A was amplified using primers specific for murine G2A and fused in frame with GFP in the pEGFP-N1 vector. The expression of the Mu-G2A-GFP fusion protein was confirmed by FACS analysis. The fusion protein will allow following the expression of murine G2A in mammalian cells and functional analysis of the G2A. Similarly, for pEGF-Hu-G2A-GFP, human G2A was fused to the N-terminal green fluorescence protein (GFP) in the pEGFP vector. The human G2A is amplified using primers specific for human G2A and fused in frame with GFP in the pEGFP vector. The fusion protein allows following the expression of human G2A in mammalian cells and functional analysis of the G2A.

EXAMPLE 10

Acceleration of Leukemogenesis In Vivo By BCR-ABL

One day prior to reconstitution, severe combined inmuunodeficient (SCID) mice were sublethally irradiated with 275 rads. Whole bone marrow was isolated and infected with retrovirus as described above. Three hours post-infection, the bone marrow was injected intravenously into the tail veins of recipient SCID mice. Animals are monitored for signs of sickness over a twelve-week period. Sick mice are sacrificed and tissues are analyzed for BCR-ABL expression by Western Blotting. Blood and spleen samples are analyzed by fluorescence activated cell sorting (FACS). Blood smears are analyzed by Wright/Giemsa staining. Mice which were injected with WT BCR-ABL exhibit significantly more leukemogenesis than mice injected with the SH2 mutant.

To evaluate the effect of BCR-ABL-regulated genes on the oncogenic potential of BCR-Abl, a soft agar fibroblast colony formation assay was used. BCR-ABL confers anchorage-independent growth of rodent fibroblasts (Rat-1) in soft agar and the numbers of colonies quantitatively reflects its transformation potency (Lugo et al., *Mol. Cell. Biol.* 9:1263–1270, 1989). This assay is described below.

EXAMPLE 11

G2A Functions as a Tumor Suppressor Gene

The G2A, G2A-GFP, or G2A indicator cell lines were generated by infection of Rat-1 fibroblasts with helper-free retroviruses followed by selection in G418 (0.4 mg/ml) for approximately 1–2 weeks. The expression of G2A-GFP and GFP were confirmed by FACS analysis using a FACScan (Becton Dickinson). Transformation by various oncogenes was measured using a soft agar assay as described (Lugo et al., supra.). Briefly, the indicator cell lines were plated at a density of $6 \times 10^4$ cells/6 cm dish overnight. Infection was performed for 3 hours at 37° C. using 1 ml of virus stock with 8 μg/ml polybrene. Two days post-infection, cells were harvested and plated in agar at a density of $1 \times 10^4$ cells/6 cm dish in duplicate. Dishes were re-fed at one week and colonies were counted after three weeks. Colonies greater than 0.5 mm in diameter were scored positive.

G2A or Neo-expressing Rat-1 cell lines were also generated by retroviral infection and G418 selection, followed by superinfection with a retroviral stock expressing BCR-ABL. Similar percentages of cells were infected by BCR-ABL-expressing retroviruses as shown by FACS analysis and Western blotting.

Most of the genes isolated by the RDA screen had no discernible effects on the oncogenic potential of BCR-ABL. However, G2A strongly antagonized the ability of BCR-ABL to form colonies in soft agar. As listed in Tables 4A–B, overexpression of G2A suppressed the number of agar colonies induced by BCR-ABL p185 approximately five fold. G2A epitope-tagged with GFP still retained some ability to block BCR-ABL-mediated transformation in Rat-1 cells. G2A also blocked agar colonies induced by Gag-BTK*, an activated version of Bruton tyrosine kinase, and the transcription factor Myc. Interestingly, G2A failed to block transformation mediated by v-ABL or the serine kinase oncogene v-Mos. v-ABL and v-Mos may transform cells by mechanisms distinct from BCR-ABL, Myc and Gag-BTK*. Since BTK has been shown to play a critical role in B cell development (Tsukada et al., *Cell* 72:279–290, 1993; Rawlings et al., *Immunological. Rev.* 138, 1994), the ability of G2A to block Gag-BTK* transformation also suggests that the G2A may also be a regulator of BTK during B cell development. Similarly, overexpression of the G2A gene suppressed the transformation of bone marrow cells. In addition, in vivo tumor formation and leukemogenesis assays can be used to analyze the effect of G2A on malignant phenotypes induced by various organisms. Transfection or infection of cells in vitro, ex vivo or in vivo with expression constructs, preferably retroviral or adenoviral vector constructs, encoding G2A results in inhibition of cell proliferation. In a preferred embodiment of the invention, bone marrow is isolated from an individual with leukemia by standard methods, and the bone marrow cells are infected with the retroviral construct encoding G2A as described herein. The bone marrow is then returned to the patient. Overexpression of G2A in the bone marrow cells inhibits further leukemogenesis and results in a significant clinical improvement.

TABLE 4A

| Oncogene | Rat-1 | Rat-1/G2A |
|---|---|---|
| ϕ | 0 | 0 |
| BCR-ABL p185 | >1300 | 226 ± 40 |
| v-ABL | 552 ± 28 | 444 ± 24 |
| Myc | >1300 | 388 ± 20 |

TABLE 4B

| Oncogene | Rat-1/GFP | Rat-1/G2A-GFP |
|---|---|---|
| ∅ | 9 ± 1 | 2 ± 1 |
| BCR-ABL p185WT | >1300 | 608 ± 40 |
| v-ABL | 432 ± 64 | 496 ± 16 |
| Gag-BTK* | 88 ± 12 | 3 ± 1 |
| v-Mos | 224 ± 16 | 172 ± 20 |

Rat-1/Neo cells exhibited a prominent elongation phenotype typical of transformation by BCR-ABL. G2A blocked this gross morphological change by BCR-ABL. When these same cell populations were plated in agar, wild type BCR-ABL alone gave rise to more than 1,000 colonies after three weeks. In contrast, BCR-ABL, co-expressed with G2A, yielded more than 5-fold fewer colonies indicating that G2A antagonizes BCR-ABL-mediated transformation. Evaluation of agar colonies recovered and expanded in liquid culture by FACS analysis showed that the cells that grew in agar lose expression of G2A but not BCR-ABL. Thus, G2A has has an anti-proliferative effect on transformation.

To determine whether the G2A was involved in the regulation of cell cycle progression, Rat-1 fibroblasts were infected with retrovirus expressing G2A gene as described in the following example.

EXAMPLE 12

G2A Induces Cell Cycle Arrest in Rat-1 Cells During Mitosis

Rat-1 cells were selected with G418 (0.4 mg/ml) for one week and grown to either subconfluence or confluence. The cells were harvested by trypsinization and pelleted by centrifugation. The cells were then resuspended in Vindelov's stain (5 mM Tris, pH 7.4, 5 mM NaCl, 0.05% NP-40, 0.04 mg/ml propidium iodide, 5 µg/ml RNase) and incubated on ice for 15 min in the dark. Flow cytometric analysis was performed using FACScan (Lysis II program). As shown in Table 5, expression of G2A increases the percentage of cells in the G2/M phase of the cell cycle. Examination of Rat-1 cells expressing the G2A under the microscope revealed a higher percentage of cells with bi- or poly-nuclei (approximately 5–10% versus less than 1% observed in parental Rat-1 cells), suggesting that G2A-expressing cells were likely to be arrested at the anaphase of mitosis. Taken together, these data suggest that the G2A may function as a tumor suppressor gene and is involved in cell cycle arret during mitosis. The biological properties of the G2A share similarities with p53, a tumor suppressor gene. Both G2A and p53 negatively regulate cell growth and induce cell cycle arret. Interestingly, their expressions are both upregulated by DNA damage-inducing agents such as X-rays. The ability of certain oncogenes to induce the expression of G2A and the ability of G2A to block the oncogenic potential of these genes suggest that the G2A may comprise a self-defense mechanism for cells to counter ill-fated transformation phenotypes.

TABLE 5

|  | G1 | S | G2/M | dead cells |
|---|---|---|---|---|
| Rat-1 (subconfluent) | 60% | 14% | 25% | 1% |
| Rat-1/G2A (subconfluent) | 47% | 14% | 37% | 2% |
| Rat-1 (confluent) | 64% | 11% | 24% | 1% |
| Rat-1/G2A (confluent) | 49% | 12% | 36% | 3% |

EXAMPLE 13

G2A Blocks the Progression of Mitosis in NIH3T3 Cells

Figure 10:
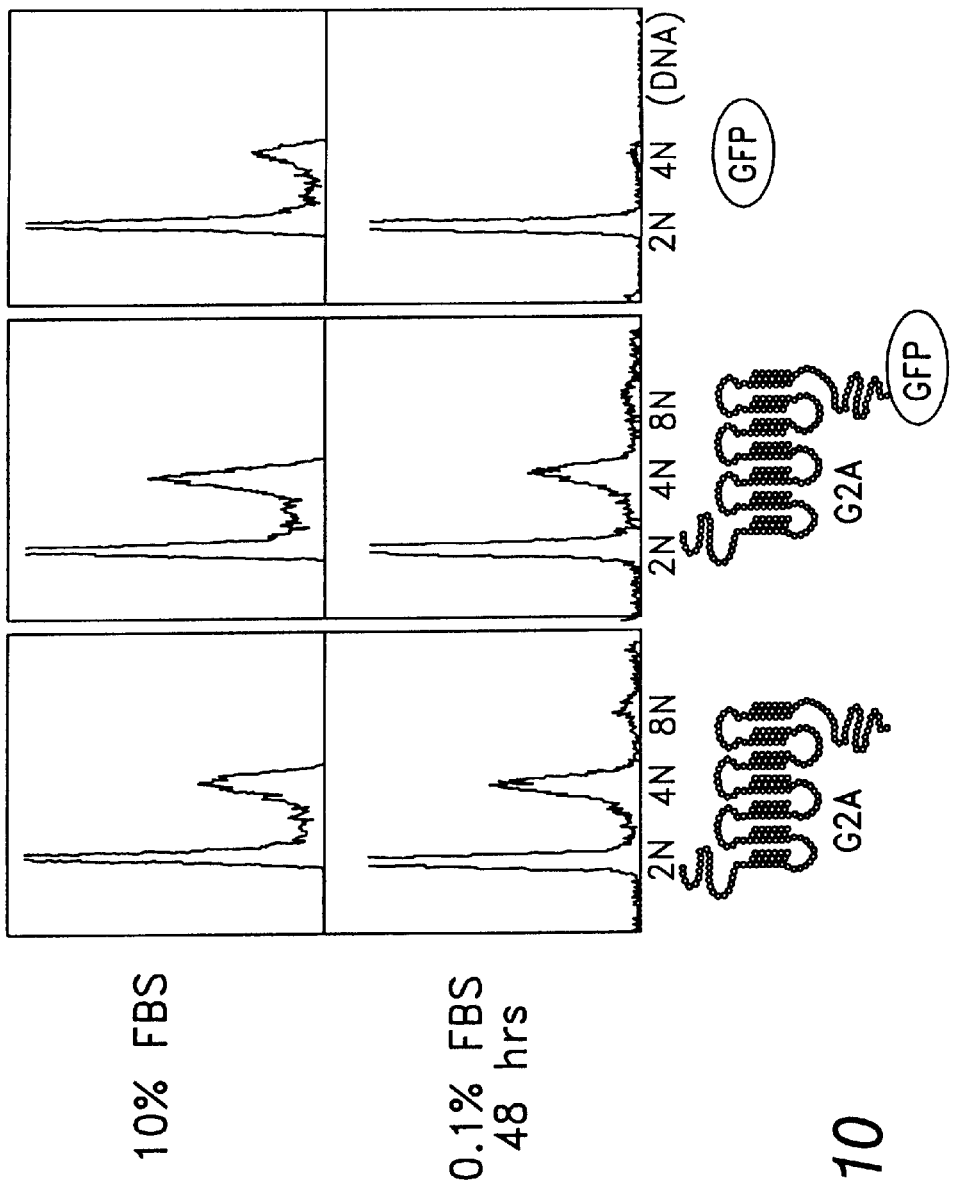
FIG. 10 shows that G2A arrests cells at the G2/M transition upon serum withdrawal.

The anti-oncogenic effect of G2A in fibroblasts and lymphoid cells, as well as the induction of G2A by cell cycle arrest-associated DNA damaging agents suggested that G2A may be involved in cell cycle regulation. To investigate this possibility, retroviruses expressing G2A, G2A-GFP fusion protein or a GFP control were used to infect NIH3T3 cells which are easily infectable (>90% of infection). Transient infection with a G2A retrovirus reproducibly increased the fractions of cells at G2/M by approximately 10% under normal growing conditions (10% FBS), strongly indicating that G2A arrests cells at G2/M. This percentage increase is comparable to that caused by overexpression of p53. To further examine whether G2A confers a G2/M block under serum starvation conditions, NIH3T3 cells expressing G2A, G2A-GFP fusion or GFP control were cultured in the presence of 0.1% FBS for 48 hours. Cells were harvested and the DNA content analyzed by FACS. Two days after serum starvation, 95% of the control cells expressing GFP alone contained 2N DNA content, suggesting that these cells were arrested at G1 upon growth factor deprivation. However, cells expressing G2A or G2A-GFP fusion protein still exhibited a large percentage of cells with 4N DNA content (39% and 34%, respectively), suggesting that G2A blocks the exit of cells from G2/M during growth factor deprivation (FIG. 10). An increase in the 8N DNA content which is accentuated during growth factor deprivation, and an increase of approximately 5–10% of multiple nuclei in cells expressing G2A or G2A-GFP, were also observed (FIG. 10). This suggests that although there is still endoduplication of DNA in cells expressing G2A, these cells failed to undergo cytokinesis suggesting a potential additional role of G2A in perturbing the mitotic spindle checkpoint.

Examination of the G2A primary sequence reveals the presence of a "destruction box" found primarily in cyclin gene products which may serve as a recognition motif for the conjugation of ubiquitin. Cytosolic ubiquitinated cyclins are degraded by the multisubunit 26S proteosome (Hochstrasser, 1996). There is some evidence that certain GPCRs such as yeast Ste2 are ubiquitinated which is required for their internalization for subsequent degradation. A more recent report demonstrated the role of ubiquitinization of a GPCR for internalization of the signal while it escaped degradation by the proteasome (Terrell et al., *Molecular Cell* 1:193–202, 1998). The presence of the "destruction box" in G2A raised the possibility that G2A may be ubiquitinated and down regulated or internalized via the ubiquitin pathway.

EXAMPLE 14

Degradation of G2A Via the Ubiguitin Pathway

Figure 11:
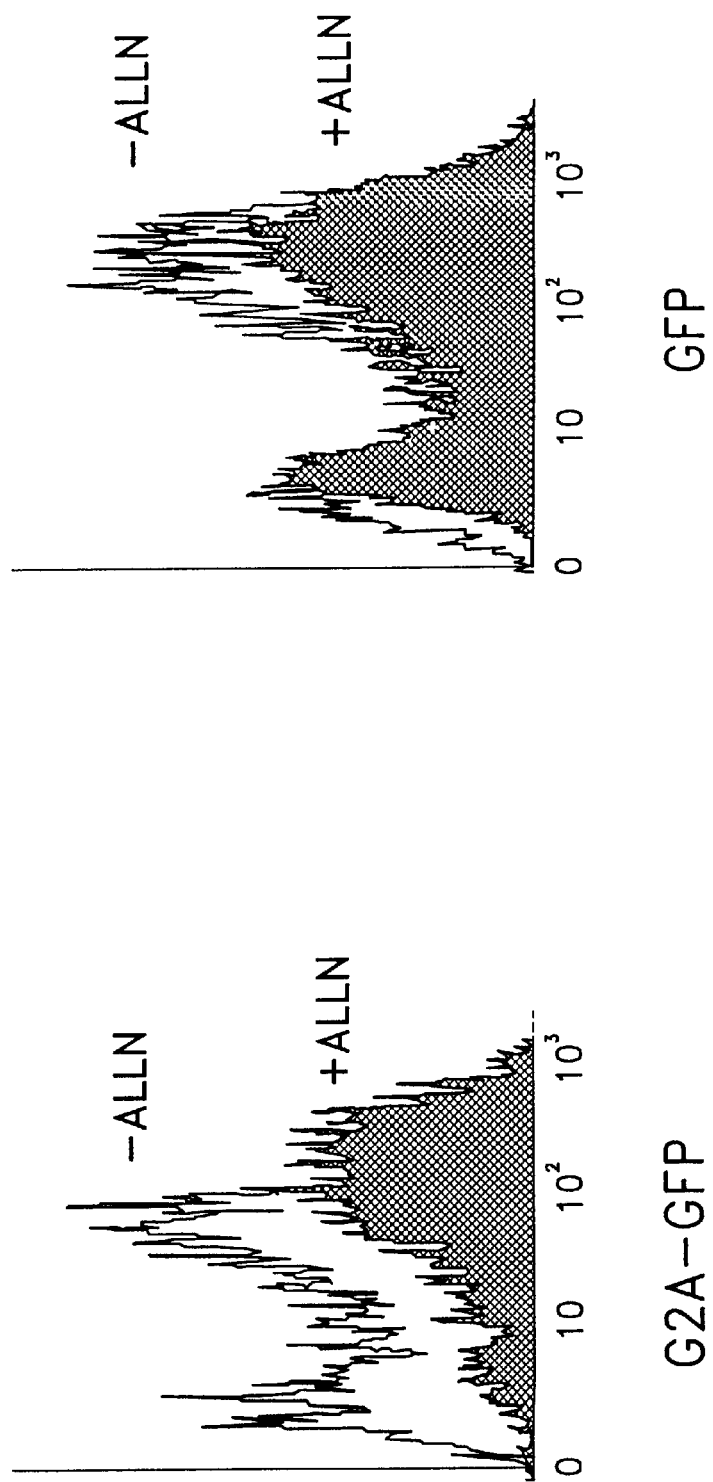
FIG. 11 is a flow cytometry profile showing that the ubiquitin-proteasome inhibitor increases the G2A protein level.
Figure 12:
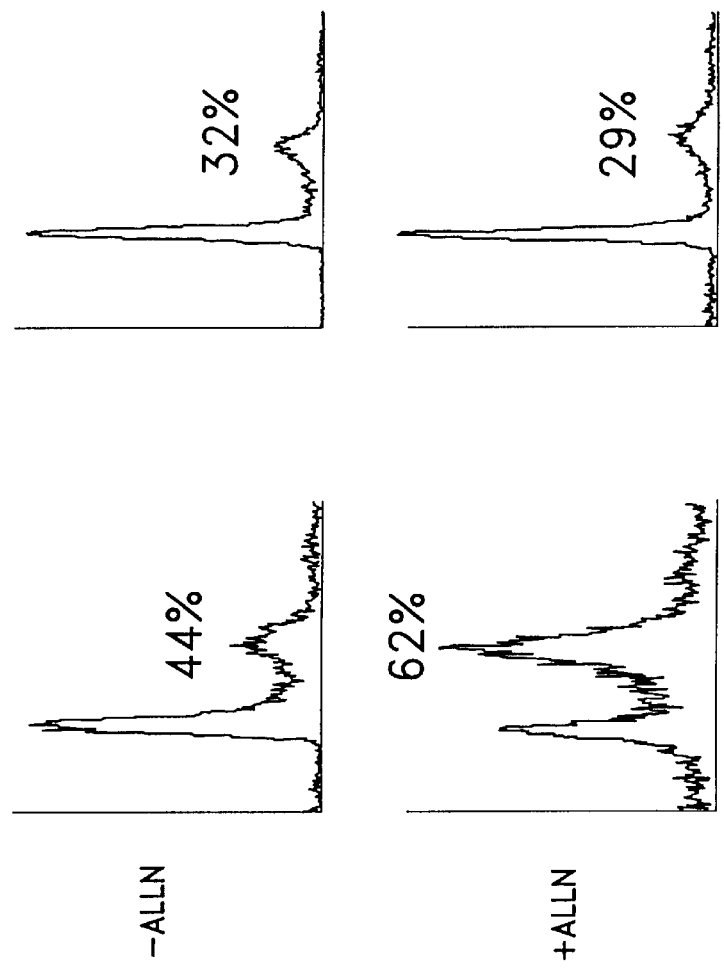
FIG. 12 shows that a ubiquitin pathway inhibitor potentiates the G2/M transition block by G2A.

N-acetyl-L-leucinyl-L-leucinyl-L-norleucinal (ALLN) is a potent inhibitor of the 20S proteasome which prevents the degradation of ubiquitinated proteins via the 20S proteasome. To determine whether the addition of ALLN can increase the protein level of G2A and potentiate the G2/M block mediated by G2A, mouse fibroblast cells were infected with retroviruses expressing G2A-GFP or GFP. After overnight incubation with a four fold lower dose of the inhibitor (50 $\mu$M) than used in previous reports, cells were harvested and analyzed by FACS for GFP. ALLN increased the protein level of G2A-GFP by 4–5 fold as measured by the log fluorescence intensity (FIG. 11). These data suggest that partial inhibition of the 20S proteasome activity stabilized or increased the overall protein level of G2A. The increased protein level of G2A by ALLN also potentiated the G2/M block (from 44% to 62%) (FIG. 12). Similar results were also obtained with another related peptide aldehyde, N-acetyl-L-leucinyl-L-leucinyl-L-methional (ALLM).

Loss of the putative "destruction box" may stabilize G2A, leading to an increase in protein level or a cellular counter-selection against an overactive G2A, leading to a decrease in overall protein level. This mutation may also result in a misfolded, non-functional receptor which is degraded even before it localizes to the plasma membrane. It is also possible that the destruction box and the ubiquitination of G2A are required for its normal function such as membrane localization, ligand activation or internalization. In addition, the ubiquitin mutant resulted in lower protein concentration.

A number of genes including p53 and Abl have been implicated in G2/M checkpoint regulation. p53 has been shown to delay the transition of G2/M by preventing the activation of Cdc25, which is required for the activation of Cdc2/Cyclin B complex. Although the precise role of Abl in the G2/M checkpoint is unknown, it has been shown that Abl physically interacts with ATM and activation of the Abl kinase activity by DNA damage is dependent on ATM. Abl is also interesting because knockout mice exhibit a lymphopenic syndrome suggesting a more significant cell cycle regulatory role in lymphoid cells than in other cell types.

EXAMPLE 15

Abl and p53 are not Required for the G2/M Block by G2A

Figure 13:
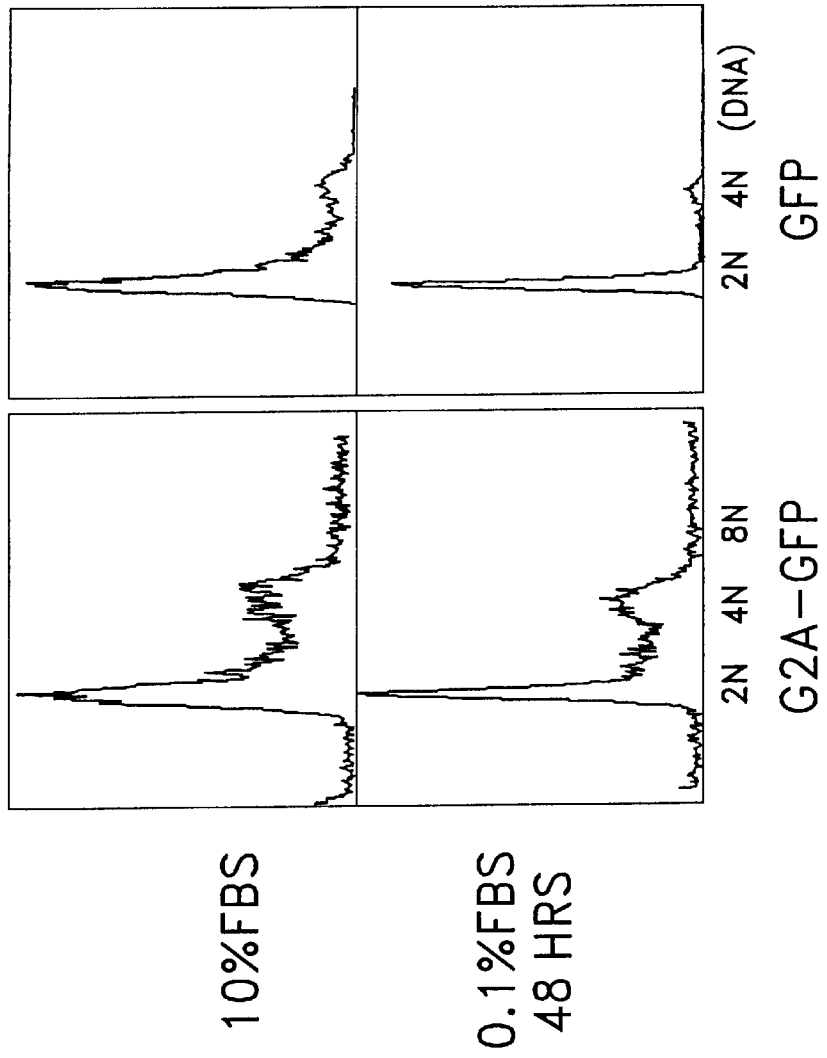
FIG. 13 shows that the G2/M block by G2A is independent of ABL.

To determine whether p53 or Abl are involved in G2A-mediated G2/M arrest, we examined whether overexpression of G2A induces G2/M arrest in fibroblasts lacking p53 or Abl. In an Abl knockout cell line, overexpression of G2A-GFP increased the percentage of cells at G2/M by approximately 15% in the presence of 10% FBS when compared to NIH3T3 cells (FIG. 13). A high percentage of cells expressing G2A were still arrested at G2/M (39%) after serum starvation (0.1% FBS) compared to GFP-expressing cells (14%) (FIG. 13), suggesting that Abl expression is not functionally required for G2/M arrest by G2A.

Figure 14:
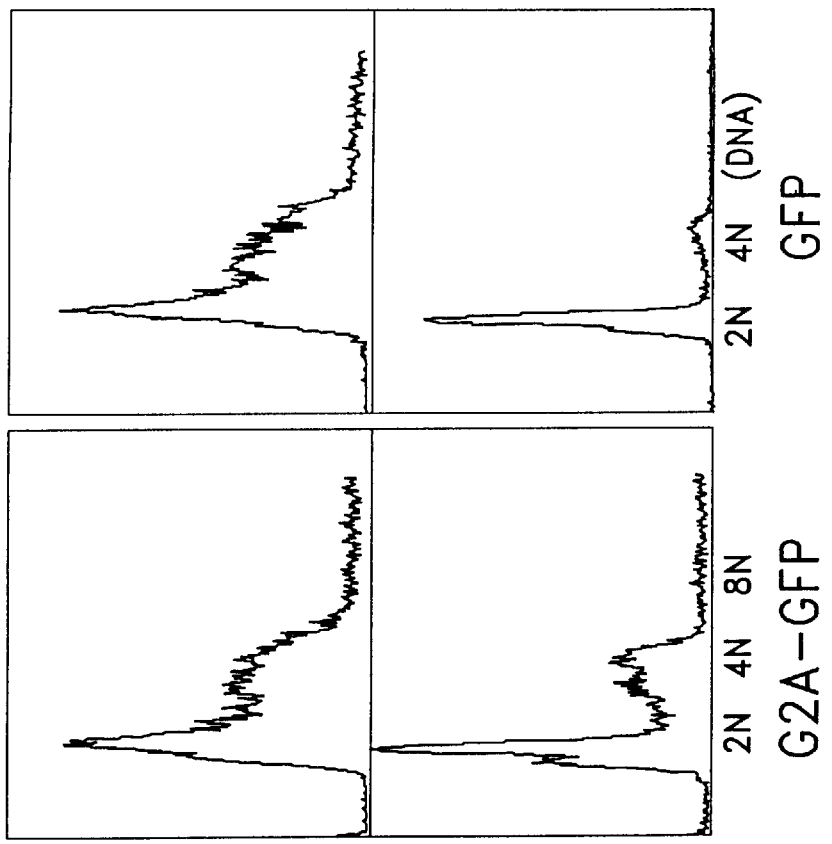
FIG. 14 shows that the G2/M block by G2A is independent of p53.

Similar experiments were preformed on a p53-/-fibroblast cell line to determine whether p53 is required for the G2/M block by G2A. FACS analysis of p53-/-fibroblasts resulted in an unusual distribution over the cell cycle consistent with the significant role of p53 as a cell cycle regulator. Overexpression of G2A in the absence of p53 did not significantly increase the percentage of cells at G2/M under normal growing conditions (10% FBS) (FIG. 14). Serum starvation for 48 hours revealed a large percentage of G2A-expressing cells still arrested at G2/M (33%) compared to GFP-expressing cells (16%) (FIG. 14), suggesting that p53 is not required for the G2/M arrest by G2A.

Since p53 is a universal sensor of DNA damage and serves as a transcription factor to induce the expression of a number of genes (such as p21, 14-3-3) in response to DNA damage, it was determined whether p53 was required for the induction of G2A in response to ionizing radiation in lymphocytes. Bone marrow cells were isolated from WT and p53-knock out mice and incubated with IL-7 and SLF (steel factor) to stimulate the outgrowth of pre-B cells. These pre-B cells were then irradiated with varying doses of X-rays. After overnight incubation following irradiation, total RNA was isolated and a semi-quantitative RT-PCR was performed as described above. The level of the G2A transcript was low in actively growing non-irradiated pre-B cells, further supporting that active proliferation signals are not sufficient to induce G2A expression. The G2A transcript was induced by X-ray in both the WT and the p53-/-mice, suggesting that the induction of G2A by gamma irradiation is not dependent on p53.

The ability of G2A to arrest the cell cycle at G2/M in the absence of p53 and abl suggested signalling via a unique pathway. To understand the molecular mechanism responsible for the G2A-mediated G2/M block, we determined whether G2A signals through the essential Maturating Promoting Factor (MPF) component Cdc2. Compounds such as caffeine have been used to reverse the DNA damage-induced inhibition of Cdc2 and release G2/M arrest. While the precise mode of action by caffeine is unknown, it has been suggested that caffeine activates Cdc25 and results in dephosphorylation of Thr14/Tyr15 in Cdc2, leading to the activation of the Cdc2/cyclin B complex and driving the completion of mitosis.

Figure 15:
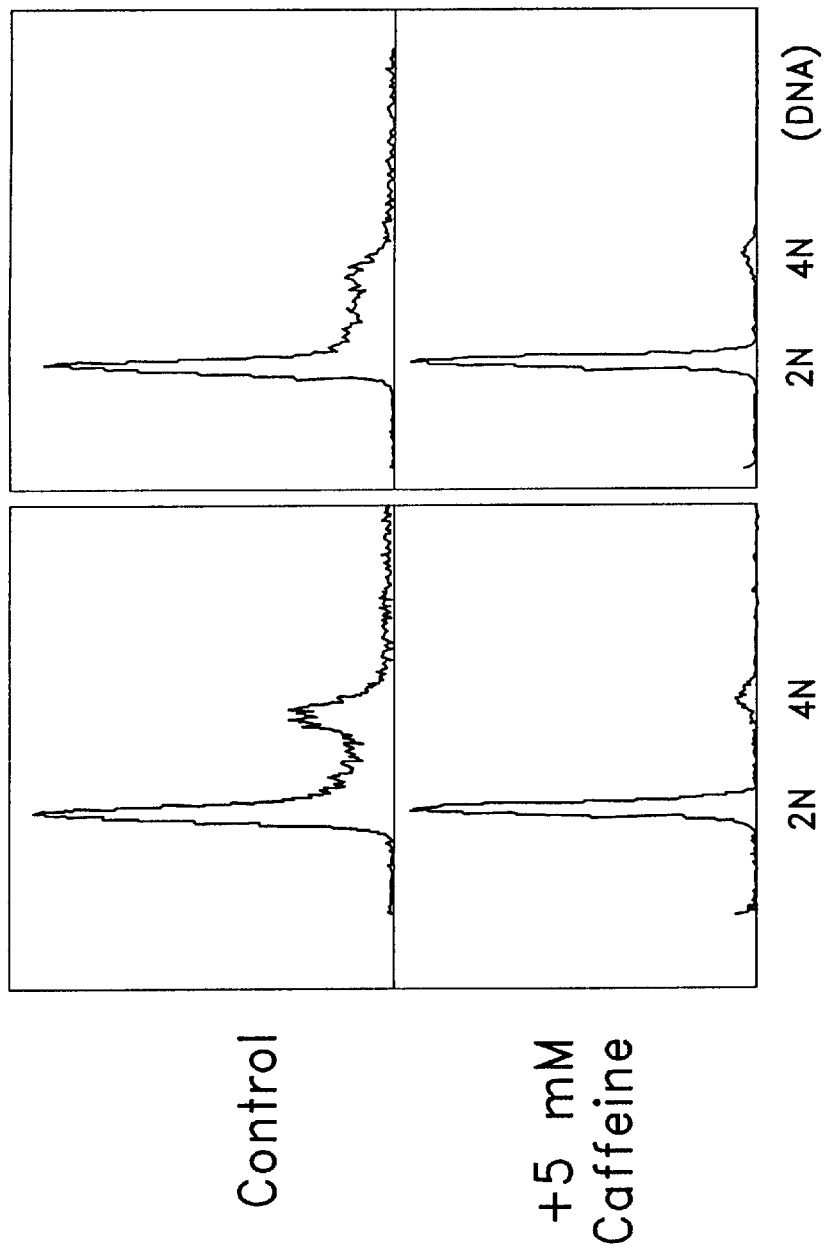
FIG. 15 shows that caffeine alleviates the G2/M block by BSA.

Mouse fibroblasts infected with retroviruses expressing a G2A-GFP fusion protein or GFP were incubated in the presence of 5 mM caffeine. The cells were harvested after overnight incubation for FACS analysis. G2A-expressing cells exhibited a high percentage at G2/M compared to GFP-expressing cells in the absence of caffeine. Overnight incubation with 5 mM caffeine relieved the G2/M arrest suggesting that the G2A-mediated G2/M block is upstream of Cdc2 (FIG. 15).

EXAMPLE 17

Chromosomal Localization of Human G2A

Fluorescence in situ hybridization (FISH) was performed using human metaphase cells prepared from phytohemagglutinin (PHA)-stimulated peripheral blood lymphocytes to determine the gene locus. The G2A probe was a human genomic fragment cloned into the Lambda DASH vector (Stratagene) at the SAll site. FISH was performed as described by Rowley et al. (*Proc. Natl. Acad. Sci. USA*. 87:9368–9372, 1990). A biotin-labeled probe was prepared by nick-translation using Bio-16-dUTP (Enzo diagnostics). Hybridization was detected with fluorescein-conjugated avidin (Vector Laboratories, Burlingame, Calif.), and chromosomes were identified by staining with 4,6-diamidino-2-phenylindole-dihydrochloride (DAPI). The human G2A was found to be localized to chromosome 14, band q32.3. It has been shown that chromosomal abnormalities at 14q32.3 are associated with a wide variety of human cancers. For example, rearrangements of bands 14q32.3 and 19p13.3 were found in patients with multiple myeloma and plasma cell leukemia (Taniwaki et al., *Leukemia and Lymphoma* 21:25–30, 1996; Fujino et al., *Cancer Res.* 55:3246–3249, 1995). In addition, deletion mapping analysis has strongly suggested that loss of a putative tumor suppressor gene at 14q32 may be involved in the pathogenesis of ovarian, endometrial, colorectal and bladder cancers (Bandera et al., *Cancer Res.* 57:513–515). Chromosomal abnormalities have also been reported at 14q32 in other human diseases such as desmoplastic infantile ganglioma and mantle cell lymphomas (Bergsagel, *Proc. Natl. Acad. Sci. U.S.A.* 93:13931–13936, 1996; Vaandrager et al., *Blood* 88:1177–1182, 1996). Based on the ability of G2A to suppress transformation phenotypes of oncogenes, G2A is a candidate tumor suppressor gene whose loss of expression may be at least partially involved in the progression of certain cancers.

It should be noted that the present invention is not limited to only those embodiments described in the Detailed Description. Any embodiment which retains the spirit of the present invention should be considered to be within its scope. However, the invention is only limited by the scope of the appended claims.

What is claimed is:

1. A method of identifying a compound which specifically binds a G protein coupled receptor G2A, wherein said G2A comprises a protein which can be expressed by a polynucleotide selected from the group consisting of SEQ ID NOS: 1 and 3, comprising the steps of:

(a) contacting said G2A receptor with a test compound; and (b) determining whether said test compound binds to said G2A receptor wherein said test compound which binds said receptor may be further screened for activation of said receptor.

2. The method of claim 1, wherein said G2A is expressed on the cell surface.

3. A method of identifying a compound which specifically binds a G protein coupled receptor G2A, wherein said G2A comprises a protein which can be expressed by a polynucleotide selected from the group consisting of SEQ ID NOS: 1 and 3, comprising the steps of:

(a) contacting said G2A receptor with a test compound; and (b) determining whether said test compound binds to said G2A receptor wherein said test compound which binds said receptor may be further screened for inhibition of said receptor.

4. The method of claim 3, wherein said G2A is expressed on the cell surface.

5. The method of claim 1, wherein said receptor has the sequence shown in SEQ ID NOS: 2 or 4.

6. The method of claim 3, wherein said receptor has the sequence shown in SEQ ID NOS: 2 or 4.

7. The method of claim 1, further comprising determining whether said test compound activates said receptor comprising the steps of:

co-infecting bone marrow cells with an oncogenic retrovirus and said G2A receptor;

contacting said bone marrow cells with said test compound;

culturing said infected bone marrow cells; and monitoring said bone marrow cells for pre-B cell growth, wherein a delay in induction of pre-B cell growth in the presence of said compound compared to the absence of said compound identifies said compound as an activator of said G2A receptor.

8. The method of claim 3, further comprising determining whether said test compound inhibits said receptor comprising the steps co-infecting bone marrow cells with an oncogenic retrovirus and said G2A receptor;

contacting said bone marrow cells with said test compound;

culturing said infected bone marrow cells; and monitoring said bone marrow cells for pre-B cell growth, wherein an acceleration in induction of pre-B cell growth in the presence of said compound compared to the absence of said compound identifies said compound as an inhibitor of said G2A receptor.

9. The method of claim 1, further comprising determining whether said test compound activates said receptor comprising the steps of:

infecting a G2A receptor-expressing cell line with an oncogenic retrovirus;

contacting said cells with said test compound;

plating said cells in agar; and determining the number of colonies greater than 0.5 mm in diameter, wherein a decrease in the number of colonies in the presence of said compound compared to the absence of said compound identifies said compound may be an activator of said receptor.

10. The method of claim 3, further comprising determining whether said test compound inhibits said receptor comprising the steps of:

infecting a G2A receptor-expressing cell line with an oncogenic retrovirus;

contacting said cells with said test compound;

plating said cells in agar; and determining the number of colonies greater than 0.5 mm in diameter, wherein a increase in the number of colonies in the presence of said compound compared to the absence of said compound identifies said compound may be an inhibitor of said receptor.

11. The method of claim 1, further comprising determining whether said test compound activates said receptor comprising the steps of:

transfecting cells with a construct encoding the G2A receptor;

contacting said cells with said test compound; and analyzing said cells by fluorescence activated cell sorting to determine the number of said cells arrested in G2/M phase, wherein an increase in said number identifies said compound as an activator of said G2A receptor.

12. The method of claim 3, further comprising determining whether said test compound inhibits said receptor comprising the steps of:

transfecting cells with a construct encoding the G2A receptor;

contacting said cells with said test compound; and analyzing said cells by fluorescence activated cell sorting to determine the number of said cells arrested in G2/M phase, wherein a decrease in said number identifies said compound as an inhibitor of said G2A receptor.

* * * * *

UNITED STATES PATENT AND TRADEMARK OFFICE
CERTIFICATE OF CORRECTION

PATENT NO. : 6,214,562 B1
DATED : April 10, 2001
INVENTOR(S) : Zhigang Weng and Owen N. Witte It is certified that error appears in the above-identified patent and that said Letters Patent is hereby corrected as shown below:

Title page,
Item [54], "REGUALTED" should read -- REGULATED --.
Item [56], References Cited, OTHER PUBLICATIONS,
Libert, et al..."fo" should read -- of --.
Bouvier, et al..."Envymology" should read -- Enzymology --; after "pp. 300-314" insert -- (1985) --.

Column 2,
Line 42, "G2m" should read -- G2/M --.

Column 8,
Line 30, after "one", "or" should read -- of --;
Line 42, "/aminopterinthymidine" should read -- /aminopterin/thymidine --.

Column 11,
Line 52, "(1995)" should read -- 1995)) --.

Column 13,
Line 60, "fill" should read -- full --.

Column 15,
Line 4, "N:" should read -- NO: --.

Column 21,
Line 41, after "has" (first occurrence) strike "has" (second occurrence);
Line 66, "arret" should read -- arrest --.

Column 22,
Line 3, "arret" should read -- arrest --.

UNITED STATES PATENT AND TRADEMARK OFFICE
CERTIFICATE OF CORRECTION

PATENT NO.    : 6,214,562 B1
DATED         : April 10, 2001
INVENTOR(S)   : Zhigang Weng and Owen N. Witte It is certified that error appears in the above-identified patent and that said Letters Patent is hereby corrected as shown below:

<u>Column 23,</u>
Line 7, "Ubiguitin" should read -- Ubiquitin --.

Signed and Sealed this

Thirty-first Day of December, 2002

JAMES E. ROGAN
*Director of the United States Patent and Trademark Office*

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 1507 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 147...1292
      (D) OTHER INFORMATION:

(xi) SEQUENCE DESCRIPTION: SEQ ID NO:1:

```
AAACCTCCCA GCTGGGCCTG CAGAGGGGTG CTCAGCCCTG CCTCAGGACG GGCCTGCCCT        60

GTGCTGCCTC AGGACTGGCT TGGGTCATTT TAAGCTGCCA GAGCCACCTT CACAAGGGGG       120

TCCACAGAAC TCACATAGGA GCCACC ATG AGA TCA GAA CCT ACC AAT GCA GCA        173
                             Met Arg Ser Glu Pro Thr Asn Ala Ala
                              1               5

GGA AAC ACC ACA CTG GGG GTT ACC TCC GTT CTT CAG AGC ACC TCA GTA        221
Gly Asn Thr Thr Leu Gly Val Thr Ser Val Leu Gln Ser Thr Ser Val
 10              15                  20                  25

CCT TCT TCT GAG ACC TGC CAC GTC TCC TAC GAG GAG AGC AGA GTG GTC        269
Pro Ser Ser Glu Thr Cys His Val Ser Tyr Glu Glu Ser Arg Val Val
                 30                  35                  40

CTG GTG GTG GTG TAC AGT GCC GTG TGC CTG CTG GGC CTA CCA GCC AAC        317
Leu Val Val Val Tyr Ser Ala Val Cys Leu Leu Gly Leu Pro Ala Asn
             45                  50                  55

TGC CTG ACT GCC TGG CTG ACG CTG CTG CAA GTC CTG CAG AGG AAC GTG        365
Cys Leu Thr Ala Trp Leu Thr Leu Leu Gln Val Leu Gln Arg Asn Val
         60                  65                  70

CTA GCC GTC TAC CTG TTC TGC CTG TCC CTC TGT GAG CTG CTC TAC ATC        413
Leu Ala Val Tyr Leu Phe Cys Leu Ser Leu Cys Glu Leu Leu Tyr Ile
     75                  80                  85

AGC ACG GTG CCA TTG TGG ATC ATC TAC ATC CAG AAT CAG CAC AAA TGG        461
Ser Thr Val Pro Leu Trp Ile Ile Tyr Ile Gln Asn Gln His Lys Trp
 90                  95                 100                 105

AAC CTG GGT CCG CAG GCC TGC AAG GTG ACT GCT TAC ATC TTC TTC TGC        509
Asn Leu Gly Pro Gln Ala Cys Lys Val Thr Ala Tyr Ile Phe Phe Cys
                110                 115                 120

AAC ATC TAC ATC AGC ATC CTC TTG CTC TGC TGC ATT TCC TGC GAC CGC        557
```

```
Asn Ile Tyr Ile Ser Ile Leu Leu Cys Cys Ile Ser Cys Asp Arg
        125                 130                 135

TAC ATG GCC GTG GTC TAT GCA CTG GAG AGC CGA GGC CAC CGC CAC CAG    605
Tyr Met Ala Val Val Tyr Ala Leu Glu Ser Arg Gly His Arg His Gln
        140                 145                 150

AGG ACT GCT GTC ACC ATT TCT GCG TGT GTG ATT CTT CTT GTT GGA CTT    653
Arg Thr Ala Val Thr Ile Ser Ala Cys Val Ile Leu Leu Val Gly Leu
        155                 160                 165

GTT AAC TAT CCA GTG TTT GAC ATG AAG GTG GAG AAG AGT TTC TGC TTT    701
Val Asn Tyr Pro Val Phe Asp Met Lys Val Glu Lys Ser Phe Cys Phe
170                 175                 180                 185

GAG CCC CTG AGG ATG AAC AGC AAG ATA GCC GGC TAC CAC TAC CTG CGT    749
Glu Pro Leu Arg Met Asn Ser Lys Ile Ala Gly Tyr His Tyr Leu Arg
                190                 195                 200

TTC ACC TTT GGC TTT GCC ATC CCT CTC GGC ATC CTG GCG TTC ACC AAT    797
Phe Thr Phe Gly Phe Ala Ile Pro Leu Gly Ile Leu Ala Phe Thr Asn
            205                 210                 215

CAC CAG ATC TTC CGG AGC ATC AAA CTC AGT GAC AGC CTG AGC GCT GCG    845
His Gln Ile Phe Arg Ser Ile Lys Leu Ser Asp Ser Leu Ser Ala Ala
            220                 225                 230

CAG AAG AAC AAG GTG AAG CGC TCC GCC ATC GCG GTC GTC ACC ATC TTC    893
Gln Lys Asn Lys Val Lys Arg Ser Ala Ile Ala Val Val Thr Ile Phe
        235                 240                 245

CTG GTC TGC TTT GCT CCC TAC CAC GTG GTA CTC CTC GTC AAA GCT GCC    941
Leu Val Cys Phe Ala Pro Tyr His Val Val Leu Leu Val Lys Ala Ala
250                 255                 260                 265

AGC TTT TCC TTC TAC CAA GGA GAC ATG GAT GCC GTG TGT GCC TTT GAA    989
Ser Phe Ser Phe Tyr Gln Gly Asp Met Asp Ala Val Cys Ala Phe Glu
                270                 275                 280

AGC AGA CTG TAC ACA GTC TCT ATG GTG TTT CTG TGC CTG TCT ACA GTC   1037
Ser Arg Leu Tyr Thr Val Ser Met Val Phe Leu Cys Leu Ser Thr Val
            285                 290                 295

AAC AGT GTG GCT GAC CCC ATC ATC TAC GTG CTG GGT ACA GAC CAC TCT   1085
Asn Ser Val Ala Asp Pro Ile Ile Tyr Val Leu Gly Thr Asp His Ser
            300                 305                 310

CGG CAA GAA GTG TCC AGA ATC CAC ACA GGG TGG AAA AAG TGG TCC ACA   1133
Arg Gln Glu Val Ser Arg Ile His Thr Gly Trp Lys Lys Trp Ser Thr
        315                 320                 325

AAG ACA TAT GTT ACA TGC TCA AAG GAC TCT GAG GAG ACA CAC TTG CCC   1181
Lys Thr Tyr Val Thr Cys Ser Lys Asp Ser Glu Glu Thr His Leu Pro
330                 335                 340                 345

ACA GAG CTT TCA AAC ACA TAC ACC TTC CCC AAT CCC GCG CAC CCT CCA   1229
Thr Glu Leu Ser Asn Thr Tyr Thr Phe Pro Asn Pro Ala His Pro Pro
                350                 355                 360

GGA TCA CAG CCA GCG AAG CTA GGT TTA CTG TGC TCG CCA GAG AGA CTG   1277
Gly Ser Gln Pro Ala Lys Leu Gly Leu Leu Cys Ser Pro Glu Arg Leu
            365                 370                 375

CCT GAG GAG CTC TGC TAAGAGACGA TTGTCCACTC TTCCTCAAAA CTAGCACCAG T 1333
Pro Glu Glu Leu Cys
            380

CACACATACC TGGTCCTCTG AGTCACCGTC TGGGGTGTCC ACAGCACTAT AGATGCCTTT   1393

GTTCGGGCAC ACGCTGCTGA TCTTTCCTTC CTAAGGCCAC CAACTCTGAA AGTATCTGTT   1453

CCTTAAACTG TCCTCAGGCT CCCCTCTATG GAAAGCGGGG CTTGCTAAGG GACC         1507
```

(2) INFORMATION FOR SEQ ID NO:2:

(i) SEQUENCE CHARACTERISTICS:
        (A) LENGTH: 382 amino acids
        (B) TYPE: amino acid (C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:2:

```
Met Arg Ser Glu Pro Thr Asn Ala Ala Gly Asn Thr Thr Leu Gly Val
 1               5                  10                  15

Thr Ser Val Leu Gln Ser Thr Ser Val Pro Ser Ser Glu Thr Cys His
            20                  25                  30

Val Ser Tyr Glu Glu Ser Arg Val Leu Val Val Val Tyr Ser Ala
            35                  40                  45

Val Cys Leu Leu Gly Leu Pro Ala Asn Cys Leu Thr Ala Trp Leu Thr
 50                  55                  60

Leu Leu Gln Val Leu Gln Arg Asn Val Leu Ala Val Tyr Leu Phe Cys
 65                  70                  75                  80

Leu Ser Leu Cys Glu Leu Leu Tyr Ile Ser Thr Val Pro Leu Trp Ile
                85                  90                  95

Ile Tyr Ile Gln Asn Gln His Lys Trp Asn Leu Gly Pro Gln Ala Cys
                100                 105                 110

Lys Val Thr Ala Tyr Ile Phe Phe Cys Asn Ile Tyr Ile Ser Ile Leu
            115                 120                 125

Leu Leu Cys Cys Ile Ser Cys Asp Arg Tyr Met Ala Val Val Tyr Ala
130                 135                 140

Leu Glu Ser Arg Gly His Arg His Gln Arg Thr Ala Val Thr Ile Ser
145                 150                 155                 160

Ala Cys Val Ile Leu Leu Val Gly Leu Val Asn Tyr Pro Val Phe Asp
                165                 170                 175

Met Lys Val Glu Lys Ser Phe Cys Phe Glu Pro Leu Arg Met Asn Ser
            180                 185                 190

Lys Ile Ala Gly Tyr His Tyr Leu Arg Phe Thr Phe Gly Phe Ala Ile
            195                 200                 205

Pro Leu Gly Ile Leu Ala Phe Thr Asn His Gln Ile Phe Arg Ser Ile
210                 215                 220

Lys Leu Ser Asp Ser Leu Ser Ala Ala Gln Lys Asn Lys Val Lys Arg
225                 230                 235                 240

Ser Ala Ile Ala Val Thr Ile Phe Leu Val Cys Phe Ala Pro Tyr
                245                 250                 255

His Val Val Leu Leu Val Lys Ala Ala Ser Phe Ser Phe Tyr Gln Gly
                260                 265                 270

Asp Met Asp Ala Val Cys Ala Phe Glu Ser Arg Leu Tyr Thr Val Ser
            275                 280                 285

Met Val Phe Leu Cys Leu Ser Thr Val Asn Ser Val Ala Asp Pro Ile
            290                 295                 300

Ile Tyr Val Leu Gly Thr Asp His Ser Arg Gln Glu Val Ser Arg Ile
305                 310                 315                 320

His Thr Gly Trp Lys Lys Trp Ser Thr Lys Thr Tyr Val Thr Cys Ser
                325                 330                 335

Lys Asp Ser Glu Glu Thr His Leu Pro Thr Glu Leu Ser Asn Thr Tyr
            340                 345                 350

Thr Phe Pro Asn Pro Ala His Pro Gly Ser Gln Pro Ala Lys Leu
            355                 360                 365

Gly Leu Leu Cys Ser Pro Glu Arg Leu Pro Glu Glu Leu Cys
```

(2) INFORMATION FOR SEQ ID NO:3:

(i) SEQUENCE CHARACTERISTICS:
        (A) LENGTH: 2938 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Coding Sequence
        (B) LOCATION: 901...2040
        (D) OTHER INFORMATION:

(xi) SEQUENCE DESCRIPTION: SEQ ID NO:3:

```
GGGAGGGGTG CNANGCTAGC CACGCAGGCG GGGCCCTGGG TCATTTTAAN CTCTCAGAGT      60

GAACGTCTTG ATAGGACCGA CAANACNCAT NACNTGTACT TAGATAGCTT ATCTTANANC     120

CACNCTGANA TTGGAACCCG CAAAATATGC CNGGGAGGAA GGTGAGCAAG GACACGACA      180

CTCACCCGGA TAAACCCAAC AAGCGCAGCG AGGCTGTGGG GAAACCGGAN CCCTGCACAC     240

CGCCGGGGGA AGGTGGGCCN CCGCCACCAC CGTGGAAGAA CAGCGCGGAN GCACCCCACG     300

AGATGAGACG GAACTGCCGT GAGATCCAGC AATNCCNACT GTGGGTCTGA CCCAGGATAN     360

CGGAAAGCAG GGACGTGAAC AGCCCTCCTC ATGTTCTTGA CACCGTCATT CTCAGCAGCT     420

CAGCTAAGGC ACAGAGGCAG CCGAGCGTCT GTCAGCAGAG TCGTGGCTGA GCAGAACACG     480

CCACACGCCA CACGCCACAC GCCACACGTG CAGGATTGCT CAAGATGGAA GGCACAGTG      540

GAATATATAT ATATATTTAT ATTTTTGGCG AGACCCTGGA GGACACACTG AATACAATGG     600

AATACCATCC CGCCTTTGAA AGGAAGGGAA ATCCTGGCAC ACGCTGCAAC AGGAGGGAGC     660

TTGAGGACAC TGTGGTGAGT GGAGCACGTG AGACACGGAA GGACACACGC TGAAGACACG     720

CAGAGATGCC CACCCACGTG GGGAGGTGAC AGGGGAGCCC AGCGCACAGA GACAAAGTGG     780

AATGGAGGCC TGGGGCTGG  GAGCAAATGC GGAGCGAGTG CTTCCTGGGG CAGAGTCTCC     840

GTTTGGGAAG ATGAGAAGGT TCTGCCGACG GATGCTGGCG ATGGTTGCAG AAGAATGTGA     900

ATG TGC CCA ATG CTA CTG AAA AAC GGT TAC AAT GGA AAC GCC ACC CCA       948
Met Cys Pro Met Leu Leu Lys Asn Gly Tyr Asn Gly Asn Ala Thr Pro
 1               5                  10                  15

GTG ACC ACC ACT GCC CCG TGG GCC TCC CTG GGC CTC TCC GCC AAG ACC       996
Val Thr Thr Thr Ala Pro Trp Ala Ser Leu Gly Leu Ser Ala Lys Thr
                20                  25                  30

TGC AAC AAC GTG TCC TTC GAA GAG AGC AGG ATA GTC CTG GTC GTG GTG      1044
Cys Asn Asn Val Ser Phe Glu Glu Ser Arg Ile Val Leu Val Val Val
             35                  40                  45

TAC AGC GCG GTG TGC ACG CTG GGG GTG CCG GCC AAC TGC CTG ACT GCG      1092
Tyr Ser Ala Val Cys Thr Leu Gly Val Pro Ala Asn Cys Leu Thr Ala
 50                  55                  60

TGG CTG GCG CTG CTG CAG GTA CTG CAG GGC AAC GTG CTG GCC GTC TAC      1140
Trp Leu Ala Leu Leu Gln Val Leu Gln Gly Asn Val Leu Ala Val Tyr
 65                  70                  75                  80

CTG CTC TGC CTG GCA CTC TGC GAG CTG CTG TAC ACA GGC ACG CTG CCA      1188
Leu Leu Cys Leu Ala Leu Cys Glu Leu Leu Tyr Thr Gly Thr Leu Pro
                 85                  90                  95

CTC TGG GTC ATC TAT ATC CGC AAC CAG CAC CGC TGG ACC CTA GGC CTG      1236
Leu Trp Val Ile Tyr Ile Arg Asn Gln His Arg Trp Thr Leu Gly Leu
                100                 105                 110

CTG GCC TGC AAG GTG ACC GCC TAC ATC TTC TTC TGC AAC ATC TAC GTC      1284
```

```
Leu Ala Cys Lys Val Thr Ala Tyr Ile Phe Phe Cys Asn Ile Tyr Val
        115                 120                 125

AGC ATC CTC TTC CTG TGC TGC ATC TCC TGC GAC CGC TTC GTG GCC GTG        1332
Ser Ile Leu Phe Leu Cys Cys Ile Ser Cys Asp Arg Phe Val Ala Val
130                 135                 140

GTG TAC GCG CTG GAG AGT CGG GGC CGC CGC CGC CGG AGG ACC GCC ATC        1380
Val Tyr Ala Leu Glu Ser Arg Gly Arg Arg Arg Arg Arg Thr Ala Ile
145                 150                 155                 160

CTC ATC TCC GCC TGC ATC TTC ATC CTC GTC GGG ATC GTT CAC TAC CCG        1428
Leu Ile Ser Ala Cys Ile Phe Ile Leu Val Gly Ile Val His Tyr Pro
                165                 170                 175

GTG TTC CAG ACG GAA GAC AAG GAG ACC TGC TTT GAC ATG CTG CAG ATG        1476
Val Phe Gln Thr Glu Asp Lys Glu Thr Cys Phe Asp Met Leu Gln Met
            180                 185                 190

GAC AGC AGG ATT GCC GGG TAC TAC TAC GCC AGG TTC ACC GTT GGC TTT        1524
Asp Ser Arg Ile Ala Gly Tyr Tyr Tyr Ala Arg Phe Thr Val Gly Phe
        195                 200                 205

GCC ATC CCT CTC TCC ATC ATC GCC TTC ACC AAC CAC CGG ATT TTC AGG        1572
Ala Ile Pro Leu Ser Ile Ile Ala Phe Thr Asn His Arg Ile Phe Arg
    210                 215                 220

AGC ATC AAG CAG AGC ATG GGC TTA AGC GCT GCC CAG AAG GCC AAG GTG        1620
Ser Ile Lys Gln Ser Met Gly Leu Ser Ala Ala Gln Lys Ala Lys Val
225                 230                 235                 240

AAG CAC TCG GCC ATC GCG GTG GTT GTC ATC TTC CTA GTC TGC TTC GCC        1668
Lys His Ser Ala Ile Ala Val Val Val Ile Phe Leu Val Cys Phe Ala
                245                 250                 255

CCG TAC CAC CTG GTT CTC CTC GTC AAA GCC GCT GCC TTT TCC TAC TAC        1716
Pro Tyr His Leu Val Leu Leu Val Lys Ala Ala Ala Phe Ser Tyr Tyr
            260                 265                 270

AGA GGA GAC AGG AAC GCC ATG TGC GGC TTG GAG GAA AGG CTG TAC ACA        1764
Arg Gly Asp Arg Asn Ala Met Cys Gly Leu Glu Glu Arg Leu Tyr Thr
        275                 280                 285

GCC TCT GTG GTG TTT CTG TGC CTG TCC ACG GTG AAC GGC GTG GCT GAC        1812
Ala Ser Val Val Phe Leu Cys Leu Ser Thr Val Asn Gly Val Ala Asp
    290                 295                 300

CCC ATT ATC TAC GTG CTG GCC ACG GAC CAT TCC CGC CAA GAA GTG TCC        1860
Pro Ile Ile Tyr Val Leu Ala Thr Asp His Ser Arg Gln Glu Val Ser
305                 310                 315                 320

AGA ATC CAT AAG GGG TGG AAA GAG TGG TCC ATG AAG ACA GAC GTC ACC        1908
Arg Ile His Lys Gly Trp Lys Glu Trp Ser Met Lys Thr Asp Val Thr
                325                 330                 335

AGG CTC ACC CAC AGC AGG GAC ACC GAG GAG CTG CAG TCG CCC GTG GCC        1956
Arg Leu Thr His Ser Arg Asp Thr Glu Glu Leu Gln Ser Pro Val Ala
            340                 345                 350

CTT GCA GAC CAC TAC ACC TTC TCC AGG CCC GTG CAC CCA CCA GGG TCA        2004
Leu Ala Asp His Tyr Thr Phe Ser Arg Pro Val His Pro Pro Gly Ser
        355                 360                 365

CCA TGC CCT GCA AAG AGG CTG ATT GAG GAG TCC TGC TGAGCCCACT GTGTGG      2056
Pro Cys Pro Ala Lys Arg Leu Ile Glu Glu Ser Cys
    370                 375                 380

CAGGGGATG GCAGGTTGGG GGTCCTGGGG CCAGCAATGT GGTTCCTGTG CACTGAGCCC       2116

ACCAGCCACA GTGCCCATGT CCCCTCTGGA AGACAAACTA CCAATTTCTC GTTCCTGAAG      2176

CCACTCCCTC CGTGACCACT GGCCCCANGC TTTCCCACAT GGAAGGTGGC TGCATGCCAA      2236

GGGGAAGAAC GACACCTCCA GGCTTCCGGG AGCCCANANA NCATGTGGCA NGCAGTGGGG      2296

CCTCTTCATC ATCANCCTGC CTGGCTGGCT CCCTTGGCTG TGGGCANGTA CACCCCTGCT      2356

GGCANAAGTA CCTGGTGGCT GCCCTGTTCG CATCANTGGC GATNACTTTA TTTGCGGAGC      2416
```

```
ATTTCTGCAA NCGTTGCCTG GATNCGGTGG TGCATTGTGG GCCCTCTGGG CTCCTGCCTC    2476

AAAATGTCAG TGANCACCAT GCTGGAAGTC ACCATCACTG TGGCANCGCC CANGAAGGCA    2536

TANGGCACCT ACCACCTCCA ANGGGGCANG CGCCCTCATC TGGGGTTGGG TCTNTTGCTG    2596

AACTGGGAAG GCCTCTANGG GAACCCTGGG GCANGGTGGC CAACTGCTNG CTCCCANAAA    2656

CCAACCCAAG GCGTCTCAAC GGGGGAACCC CAAATGTTCN CGCCCCANAA AAAACAATTT    2716

TNGGAAGGAN AAGTTNTTAA ACACCCCNCC NCCANAAGCC AAGGGGTTCC CAGGAAATTC    2776

CCCACCGGCA TCCTCCGGGG AAAANACTCG GTNAANGGGT CCCTTACAAG GGTTGGGGGT    2836

TCCCCNCCCC TAACCCCCNT TAATTGAAGG GGGGGAAATT CAACCCTTTT GGCCTCCTTT    2896

TTTTTTGCGG NAAAAAAAC AACNTCCCCT GCANCCCCCG GN                        2938
```

(2) INFORMATION FOR SEQ ID NO:4:

(i) SEQUENCE CHARACTERISTICS:
        (A) LENGTH: 380 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Met Cys Pro Met Leu Leu Lys Asn Gly Tyr Asn Gly Asn Ala Thr Pro
 1               5                  10                  15

Val Thr Thr Thr Ala Pro Trp Ala Ser Leu Gly Leu Ser Ala Lys Thr
                20                  25                  30

Cys Asn Asn Val Ser Phe Glu Glu Ser Arg Ile Val Leu Val Val Val
            35                  40                  45

Tyr Ser Ala Val Cys Thr Leu Gly Val Pro Ala Asn Cys Leu Thr Ala
        50                  55                  60

Trp Leu Ala Leu Leu Gln Val Leu Gln Gly Asn Val Leu Ala Val Tyr
65                  70                  75                  80

Leu Leu Cys Leu Ala Leu Cys Glu Leu Leu Tyr Thr Gly Thr Leu Pro
                85                  90                  95

Leu Trp Val Ile Tyr Ile Arg Asn Gln His Arg Trp Thr Leu Gly Leu
                100                 105                 110

Leu Ala Cys Lys Val Thr Ala Tyr Ile Phe Phe Cys Asn Ile Tyr Val
            115                 120                 125

Ser Ile Leu Phe Leu Cys Cys Ile Ser Cys Asp Arg Phe Val Ala Val
        130                 135                 140

Val Tyr Ala Leu Glu Ser Arg Gly Arg Arg Arg Arg Thr Ala Ile
145                 150                 155                 160

Leu Ile Ser Ala Cys Ile Phe Ile Leu Val Gly Ile Val His Tyr Pro
                165                 170                 175

Val Phe Gln Thr Glu Asp Lys Glu Thr Cys Phe Asp Met Leu Gln Met
                180                 185                 190

Asp Ser Arg Ile Ala Gly Tyr Tyr Ala Arg Phe Thr Val Gly Phe
        195                 200                 205

Ala Ile Pro Leu Ser Ile Ile Ala Phe Thr Asn His Arg Ile Phe Arg
    210                 215                 220

Ser Ile Lys Gln Ser Met Gly Leu Ser Ala Ala Gln Lys Ala Lys Val
225                 230                 235                 240

Lys His Ser Ala Ile Ala Val Val Val Ile Phe Leu Val Cys Phe Ala
```

```
                       245                 250                 255
Pro Tyr His Leu Val Leu Val Lys Ala Ala Ala Phe Ser Tyr Tyr
            260                 265                 270

Arg Gly Asp Arg Asn Ala Met Cys Gly Leu Glu Glu Arg Leu Tyr Thr
            275                 280                 285

Ala Ser Val Val Phe Leu Cys Leu Ser Thr Val Asn Gly Val Ala Asp
            290                 295                 300

Pro Ile Ile Tyr Val Leu Ala Thr Asp His Ser Arg Gln Glu Val Ser
305                 310                 315                 320

Arg Ile His Lys Gly Trp Lys Glu Trp Ser Met Lys Thr Asp Val Thr
                325                 330                 335

Arg Leu Thr His Ser Arg Asp Thr Glu Glu Leu Gln Ser Pro Val Ala
            340                 345                 350

Leu Ala Asp His Tyr Thr Phe Ser Arg Pro Val His Pro Pro Gly Ser
            355                 360                 365

Pro Cys Pro Ala Lys Arg Leu Ile Glu Glu Ser Cys
370                 375                 380
```

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Lys Asp Ser Glu Glu Thr His Leu Pro Thr Glu Leu Ser
1               5                   10
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

AGCACTCTCC AGCCTCTCAC CGCA     24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

ACCGACGTCG ACTATCCATG AACA     24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

```
AGGCAACTGT GCTATCCGAG GGAA                                               24

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:9:

GATCTGCGGT GA                                                            12

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:10:

GATCTGTTCA TG                                                            12

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:11:

GATCTTCCCT CG                                                            12

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

CAGGACTGGC TTGGGTCATT                                                    20

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

GTCCACAGAA CTCACATAGG A                                                  21

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:14:

CGCGGATCCG AATTCGGTAC CGGTGACTCA GAGGACCAG                                39
```

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:15:

CGGAATTCTC GAGTCAGGAC TGGCTTGGGT CATT                      34

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:16:

ATAGTTTAGC GGCCGCGCAG AGCTCCTCAG GCAGT                     35

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

CAAGAAGTGT CCAGAATCCA                                  20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:18:

GGTGACAGCA GTCCTCTGGT                                  20

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

TAGCGGTCGC AGGAAATGCA G                                21

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:20:

TGATTGGTGA ACGCCAGG                                    18

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:21:

GCTTTGAGCC CCTGAGGATG AA                              22

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:22:

GTAATACGAC TCACTATAGG GC                              22

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:23:

GTCGGATCCA TGAGATCAGA ACCTACCAAT                      30

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:24:

GTCGAATTCT CACAGGACCA CTCTGCTCTC                      30

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:25:

CAGGAAACAG CTATGAC                                    17

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:26:

CUACUACUAC UAGGCCACGC GTCGACTAGT ACGGGGGGGG GG          42

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:27:

```
GCCGAATTCT CAAACTCCGG C                                            21
```

(2) INFORMATION FOR SEQ ID NO:28:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:28:

```
CCGGAATTCG GCCACCATGG ACTACAAGGA CGACGATGAC AAGAGATCAG AACCTACCAA   60

TGCA                                                               64
```

(2) INFORMATION FOR SEQ ID NO:29:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:29:

```
CCGGAATTCC TAGAGGCCAC CATGAGATCA GAACCTACCA AT                     42
```

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:30:

```
CGCTCGAGTG GGAGCAAATG CGGAGCGAG                                    29
```

(2) INFORMATION FOR SEQ ID NO:31:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:31:

```
TTAGCGGCCG CTCAGCAGGA CTCCTCAATC AG                                32
```

(2) INFORMATION FOR SEQ ID NO:32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:32:

```
TTAGCGGCCG CGCAGGACTC CTCAATCAGC CTC                               33
```

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:33:

CAAGAAGTGT CCAGAATCCA                                                    20

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:34:

ACCAGCCACA GTGCCCATG                                                     19

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:35:

TGCCACTCTG GGTCATCTAT                                                    20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:36:

CGGTGGTTGT CATCTTCCTA                                                    20

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:37:

GTAATACGAC TCACTATAGG GC                                               22

(2) INFORMATION FOR SEQ ID NO:38:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:38:

CAGGAAACAG CTATGAC                                                       17

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:39:

ACCACAGTCC ATGCCATCAC       20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:40:

TCCACCACCC TGTTGCTGTA       20